(12) United States Patent
Schmitt et al.

(10) Patent No.: US 10,710,889 B2
(45) Date of Patent: Jul. 14, 2020

(54) EMM-31 MATERIALS AND PROCESSES AND USES THEREOF

(71) Applicant: ExxonMobil Research and Engineering Company, Annandale, NJ (US)

(72) Inventors: Kirk D. Schmitt, Pennington, NJ (US); Allen W. Burton, Stewartsville, NJ (US); Hilda B. Vroman, Piscataway, NJ (US); Karl G. Strohmaier, Port Murray, NJ (US); Simon C. Weston, Annandale, NJ (US); Michael A. Marella, Easton, PA (US); Ross Mabon, Whitehall, PA (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 0 days.

(21) Appl. No.: 16/190,396

(22) Filed: Nov. 14, 2018

(65) Prior Publication Data

US 2019/0194028 A1    Jun. 27, 2019

Related U.S. Application Data

(60) Provisional application No. 62/608,602, filed on Dec. 21, 2017.

(51) Int. Cl.
| | | |
|---|---|---|
| *C01B 39/48* | (2006.01) |
| *B01J 29/70* | (2006.01) |
| *C01B 39/12* | (2006.01) |
| *C07D 207/06* | (2006.01) |
| *B01J 35/00* | (2006.01) |
| *C07D 295/037* | (2006.01) |
| *B01J 29/74* | (2006.01) |
| *B01J 29/86* | (2006.01) |

(52) U.S. Cl.
CPC ............ *C01B 39/48* (2013.01); *B01J 29/70* (2013.01); *B01J 29/74* (2013.01); *B01J 29/86* (2013.01); *B01J 35/002* (2013.01); *C01B 39/12* (2013.01); *C07D 207/06* (2013.01); *C07D 295/037* (2013.01); *B01J 2229/186* (2013.01); *B01J 2229/42* (2013.01); *C01P 2002/30* (2013.01); *C01P 2002/72* (2013.01); *C01P 2002/77* (2013.01)

(58) Field of Classification Search
CPC .......... C01B 39/48; C01B 39/12; B01J 29/70; B01J 29/86; C01P 2002/72; C01P 2002/77; C07D 207/06
See application file for complete search history.

(56) References Cited

U.S. PATENT DOCUMENTS

| 7,648,694 B2 | 1/2010 | Burton, Jr. |
| 10,252,918 B2 * | 4/2019 | Schmitt .................. C01B 39/48 |
| 2017/0158521 A1 | 6/2017 | Schmitt et al. |

OTHER PUBLICATIONS https://america.iza-structure.org/IZA-SC/pow_plot_VerifSyn.php?STC=MWW&patternFN=MWW_KPL_MCM22.csv Downloaded Nov. 25, 2019 (Year: 1998).*

(Continued)

*Primary Examiner* — David M Brunsman
(74) *Attorney, Agent, or Firm* — Priya G. Prasad

(57) ABSTRACT

The disclosure is related to EMM-31 materials, processes, and uses of the same as well as reagents used in the preparation of the EMM-31 materials, process and intermediates for preparing these reagents.

29 Claims, 2 Drawing Sheets

(56) References Cited

OTHER PUBLICATIONS

"Atlas of Zeolite Framework Types", eds Ch. Baerlocher, L.B. McCusker, and D.H. Olson, Elsevier, Sixth Edition, 2007.
Zhegalova et al., "Wolff rearrangement of B-alkynyl-a-diazo-B-ketoesters: light-induced acetylene-allene somerization and its use for activation of enediynes", J. Phys. Org. Chem., 2011, 24 969-975.
Simon, "Ion Exchange Training Manural", Springer Science + Business Media, 1991.
Weisz et al., "Superactive Crystallline Aluminosilicate Hydrocarbon Catalysts", J. Catalysis., 1965, 4, 527-529.
Miale et al., "Catalysis by Crystalline Aluminosilicates", J. Catalysis., 1966, 6, 278-287.
Olson et al., "Chemical and Physical Properties of the ZSM-5 Substitutional Series", J. Catalysis., 1980, 61, 390-396.
Lippens et al., "Studies on Pore Systems in Catalysts", J. Catalysis, 1965, 4, 319-323.
The International Search Report and Written Opinion of PCT/US2018/060916 dated Apr. 5, 2019.

\* cited by examiner

EMM-31 MATERIALS AND PROCESSES AND USES THEREOF

CROSS-REFERENCE TO RELATED APPLICATIONS

This application claims priority to U.S. Provisional Application Ser. No. 62/608,602 filed Dec. 21, 2017, which is herein incorporated by reference in its entirety.

TECHNICAL FIELD

This disclosure relates to materials designated as EMM-31, processes of making such materials, uses of these materials, reagents employed in making such materials, and process and intermediates for preparing the reagents.

BACKGROUND

Zeolites can be used as adsorbents and catalysts or support for catalysts for hydrocarbon conversions. Zeolites have uniform cavities and pores that are interconnected by channels. The sizes and dimensions of cavities and the pores allow for adsorption of molecules of certain sizes. Due to their ability to adsorb molecules through size selections, zeolites have many uses including hydrocarbon conversions, e.g., cracking, hydrocracking, disproportionation, alkylation, oligomerization, and isomerization.

Zeolites that find application in catalysis include any of the naturally occurring or synthetic crystalline zeolites. Examples of these zeolites include large pore zeolites, intermediate pore size zeolites, and small pore zeolites. These zeolites and their isotypes are described in "Atlas of Zeolite Framework Types", eds. Ch. Baerlocher, L. B. McCusker, and D. H. Olson, Elsevier, Sixth Edition, 2007, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON frame-work type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

Even the smallest changes in pore topology, size and shape can greatly affect sorption selectivity and catalytic activity and selectivity thus new zeolites are highly sought after.

SUMMARY

This disclosure provides EMM-31 crystalline materials, processes of preparing these materials, uses thereof, reagents employed in making such materials, and process and intermediates for preparing the reagents. In one aspect, the disclosure provides crystalline materials (where part or all of the SDA has been removed) having at least six X-ray diffraction (XRD) peaks in degree 2-theta selected from Table 1:

TABLE 1

| degree 2-theta (±0.2) | relative intensity [100 × I/(Io)] |
|---|---|
| 6.39 | 60-100 |
| 7.78 | 60-80 |
| 8.22 | 20-40 |
| 8.82 | 20-40 |
| 9.34 | 10-30 |
| 9.89 | 5-25 |
| 13.31 | 20-40 |
| 19.40 | 60-100 |
| 23.13 | 60-90 |
| 23.71 | 15-35 |

In a further aspect, provided herein is a crystalline material having a framework defined by the following connectivities in Table 2 for the tetrahedral (T) atoms in the unit cell, the tetrahedral (T) atoms being connected by bridging atoms:

TABLE 2

| T atom | Connected to: |
|---|---|
| T1 | T2, T4, T37, T100 |
| T2 | T1, T3, T6, T57 |
| T3 | T2, T5, T56, T99 |
| T4 | T1, T64, T95, T121 |
| T5 | T3, T6, T65, T94 |
| T6 | T2, T5, T66, T126 |
| T7 | T8, T10, T43, T104 |
| T8 | T7, T9, T12, T51 |
| T9 | T8, T11, T50, T103 |
| T10 | T7, T70, T89, T125 |
| T11 | T9, T12, T71, T88 |
| T12 | T8, T11, T72, T122 |
| T13 | T14, T16, T25, T108 |
| T14 | T13, T15, T18, T69 |
| T15 | T14, T17, T68, T107 |
| T16 | T13, T52, T83, T113 |
| T17 | T15, T18, T53, T82 |
| T18 | T14, T17, T54, T118 |
| T19 | T20, T22, T31, T112 |
| T20 | T19, T21, T24, T63 |
| T21 | T20, T23, T62, T111 |
| T22 | T19, T58, T77, T117 |
| T23 | T21, T24, T59, T76 |
| T24 | T20, T23, T60, T114 |
| T25 | T13, T26, T28, T116 |
| T26 | T25, T27, T30, T81 |
| T27 | T26, T29, T80, T115 |
| T28 | T25, T71, T88, T105 |
| T29 | T27, T30, T70, T89 |
| T30 | T26, T29, T90, T110 |
| T31 | T19, T32, T34, T120 |
| T32 | T31, T33, T36, T75 |
| T33 | T32, T35, T74, T119 |
| T34 | T31, T65, T94, T109 |
| T35 | T33, T36, T64, T95 |
| T36 | T32, T35, T96, T106 |
| T37 | T1, T38, T40, T124 |
| T38 | T37, T39, T42, T93 |
| T39 | T38, T41, T92, T123 |
| T40 | T37, T59, T76, T97 |
| T41 | T39, T42, T58, T77 |
| T42 | T38, T41, T78, T102 |
| T43 | T7, T44, T46, T128 |
| T44 | T43, T45, T48, T87 |
| T45 | T44, T47, T86, T127 |
| T46 | T43, T53, T82, T101 |
| T47 | T45, T48, T52, T83 |
| T48 | T44, T47, T84, T98 |
| T49 | T50, T52, T85, T124 |
| T50 | T9, T49, T51, T54 |
| T51 | T8, T50, T53, T123 |
| T52 | T16, T47, T49, T97 |
| T53 | T17, T46, T51, T54 |

TABLE 2-continued

| T atom | Connected to: |
|---|---|
| T54 | T18, T50, T53, T102 |
| T55 | T56, T58, T91, T128 |
| T56 | T3, T55, T57, T60 |
| T57 | T2, T56, T59, T127 |
| T58 | T22, T41, T55, T101 |
| T59 | T23, T40, T57, T60 |
| T60 | T24, T56, T59, T98 |
| T61 | T62, T64, T73, T116 |
| T62 | T21, T61, T63, T66 |
| T63 | T20, T62, T65, T115 |
| T64 | T4, T35, T61, T105 |
| T65 | T5, T34, T63, T66 |
| T66 | T6, T62, T65, T110 |
| T67 | T68, T70, T79, T120 |
| T68 | T15, T67, T69, T72 |
| T69 | T14, T68, T71, T119 |
| T70 | T10, T29, T67, T109 |
| T71 | T11, T28, T69, T72 |
| T72 | T12, T68, T71, T106 |
| T73 | T61, T74, T76, T108 |
| T74 | T33, T73, T75, T78 |
| T75 | T32, T74, T77, T107 |
| T76 | T23, T40, T73, T113 |
| T77 | T22, T41, T75, T78 |
| T78 | T42, T74, T77, T118 |
| T79 | T67, T80, T82, T112 |
| T80 | T27, T79, T81, T84 |
| T81 | T26, T80, T83, T111 |
| T82 | T17, T46, T79, T117 |
| T83 | T16, T47, T81, T84 |
| T84 | T48, T80, T83, T114 |
| T85 | T49, T86, T88, T100 |
| T86 | T45, T85, T87, T90 |
| T87 | T44, T86, T89, T99 |
| T88 | T11, T28, T85, T121 |
| T89 | T10, T29, T87, T90 |
| T90 | T30, T86, T89, T126 |
| T91 | T55, T92, T94, T104 |
| T92 | T39, T91, T93, T96 |
| T93 | T38, T92, T95, T103 |
| T94 | T5, T34, T91, T125 |
| T95 | T4, T35, T93, T96 |
| T96 | T36, T92, T95, T122 |
| T97 | T40, T52, T98, T100 |
| T98 | T48, T60, T97, T99 |
| T99 | T3, T87, T98, T100 |
| T100 | Ti, T85, T97, T99 |
| T101 | T46, T58, T102, T104 |
| T102 | T42, T54, T101, T103 |
| T103 | T9, T93, T102, T104 |
| T104 | T7, T91, T101, T103 |
| T105 | T28, T64, T106, T108 |
| T106 | T36, T72, T105, T107 |
| T107 | T15, T75, T106, T108 |
| T108 | T13, T73, T105, T107 |
| T109 | T34, T70, T110, T112 |
| T110 | T30, T66, T109, T111 |
| T111 | T21, T81, T110, T112 |
| T112 | T19, T79, T109, T111 |
| T113 | T16, T76, T114, T116 |
| T114 | T24, T84, T113, T115 |
| T115 | T27, T63, T114, T116 |
| T116 | T25, T61, T113, T115 |
| T117 | T22, T82, T118, T120 |
| T118 | T18, T78, T117, T119 |
| T119 | T33, T69, T118, T120 |
| T120 | T31, T67, T117, T119 |
| T121 | T4, T88, T122, T124 |
| T122 | T12, T96, T121, T123 |
| T123 | T39, T51, T122, T124 |
| T124 | T37, T49, T121, T123 |
| T125 | T10, T94, T126, T128 |
| T126 | T6, T90, T125, T127 |
| T127 | T45, T57, T126, T128 |
| T128 | T43, T55, T125, T127 |

In another aspect, this disclosure provides a material having Formula I:

$$(v)X_2O_3:YO_2 \quad \text{(Formula I)},$$

wherein $0.0005 \leq v \leq 0.1$, X is a trivalent element, and Y is a tetravalent element.

In yet another aspect, provided herein is an as-made crystalline material (where the SDA has not been removed) having at least six XRD peaks in degree 2-theta selected from Table 3:

TABLE 3

| degree 2-theta (±0.2) | relative intensity [100 × I/(Io)] |
|---|---|
| 6.34 | 20-60 |
| 7.75 | 10-30 |
| 8.25 | 20-60 |
| 8.71 | 20-40 |
| 9.32 | 1-20 |
| 15.47 | 1-20 |
| 19.37 | 40-80 |
| 21.40 | 40-70 |
| 22.92 | 60-100 |
| 23.51 | 20-50 |

In still yet another aspect, this disclosure provides processes of preparing the materials described herein.

In a further aspect, provided herein is Compound E, which is a structure directing agent that may be used in the preparation of the as-made EMM-31. Compound E has the following structure:

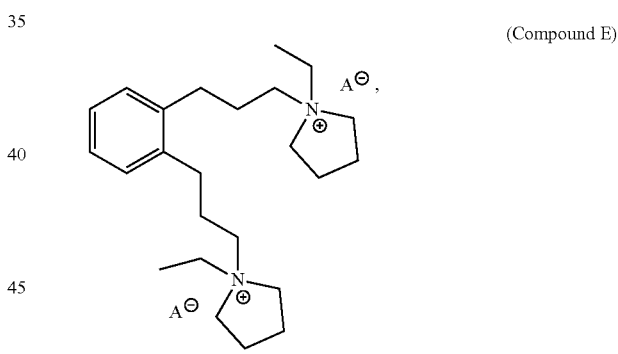

(Compound E)

wherein A is an ion. Yet in a further aspect, this disclosure also provides processes of preparing Compound E.

Any two or more of the features described in this specification, including in this summary section, can be combined to form combinations of features not specifically described herein. The details of one or more features are set forth in the accompanying drawings and the description below. Other features and advantages will be apparent from the description and drawings, and from the claims.

DETAILED DESCRIPTION

Figure 1:
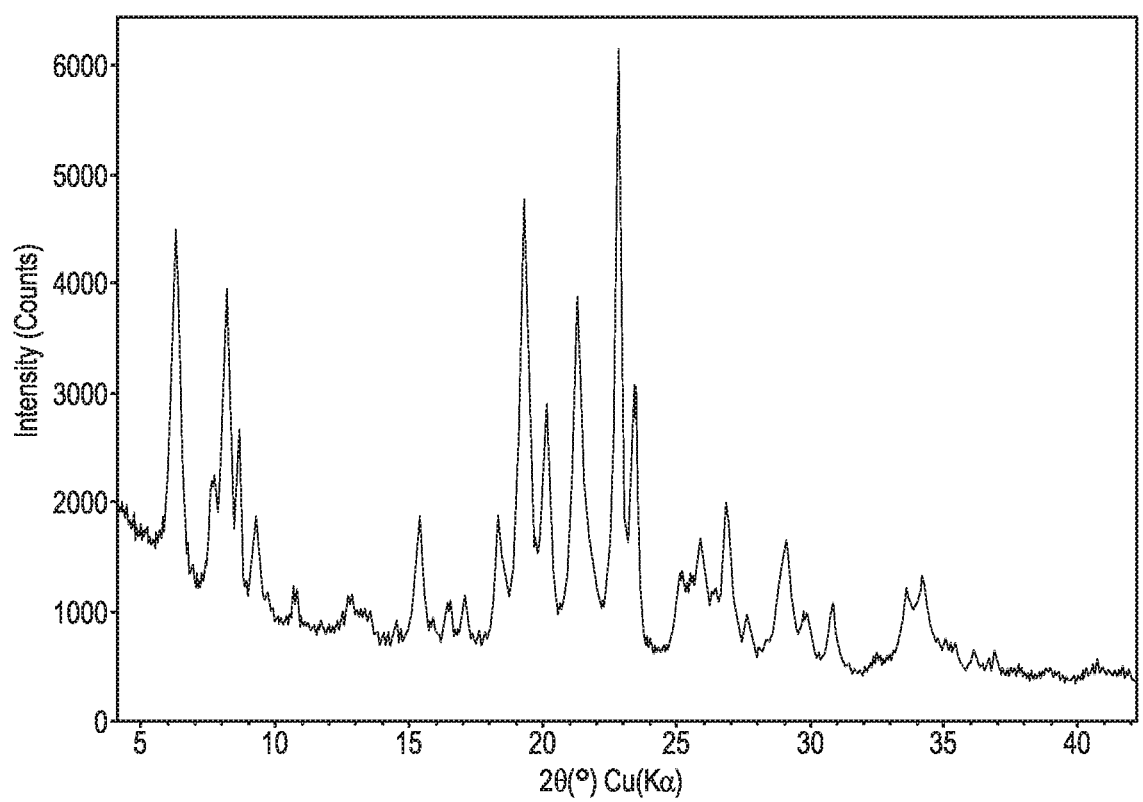
FIG. 1 shows a powder XRD pattern of an as-made EMM-31 material using a sodium-containing reagent.

Provided herein are materials designated as EMM-31, processes of preparing these materials, uses thereof, reagents such as structure directing agents for preparing EMM-31, process and intermediates for preparing the reagents. The EMM-31 where part or all of the organic template has been removed (e.g., thermal treatment or other treatment to remove the structure directing agent (SDA)) may be described as having a chemical composition of oxides of a trivalent element (e.g., $X_2O_3$) and oxides of a tetravalent element (e.g., $YO_2$), where these oxides can be in various molar ratios. X is a trivalent element and Y is a tetravalent element. The as-made EMM-31 (i.e., before thermal treatment or other treatment to remove the SDA) may include a SDA, one of the reagents of the synthesis. In one aspect, the as-made EMM-31 may be subjected to thermal treatment to remove part or all of the SDA. Thermal treatment (e.g., calcination) of the as-made EMM-31 typically exposes the materials to high temperatures, e.g., to 400-700° C., in an atmosphere selected from air, nitrogen, or a mixture thereof in a furnace. In another aspect, ozone treatment of the as-made EMM-31 may be used to remove part or all of the SDA. EMM-31 where part or all of the SDA has been removed can be used as adsorbents and catalysts or support for catalysts for hydrocarbon conversions, e.g., conversion of organic compounds to a converted product.

In one aspect, the EMM-31 material, where part of all of the SDA has been removed, has at least six XRD peaks in degree 2-theta selected from Table 1:

TABLE 1

| degree 2-theta (±0.2) | relative intensity [100 × I/(Io)] |
|---|---|
| 6.39 | 60-100 |
| 7.78 | 60-80 |
| 8.22 | 20-40 |
| 8.82 | 20-40 |
| 9.34 | 10-30 |
| 9.89 | 5-25 |
| 13.31 | 20-40 |
| 19.40 | 60-100 |
| 23.13 | 60-90 |
| 23.71 | 15-35 |

In one or more aspects, the EMM-31 materials (where part or all of the SDA has been removed) may have at least six XRD peaks with the degree 2-theta and d-spacing values selected from Table 1A, wherein the d-spacing values have a deviation determined based on the corresponding deviation ±0.20 degree 2-theta when converted to the corresponding values for d-spacing using Bragg's law:

TABLE 1A

| degree 2-theta (±0.2) | d-spacing (Å) | relative intensity [100 × I/(Io)] |
|---|---|---|
| 6.39 | 13.81 | 60-100 |
| 7.78 | 11.35 | 60-80 |
| 8.22 | 10.75 | 20-40 |
| 8.82 | 10.02 | 20-40 |
| 9.34 | 9.47 | 10-30 |
| 9.89 | 8.94 | 5-25 |
| 13.31 | 6.65 | 20-40 |
| 19.40 | 4.57 | 60-100 |
| 23.13 | 3.84 | 60-90 |
| 23.71 | 3.75 | 15-35 |

The XRD patterns with the XRD peaks described herein use $Cu(K_\alpha)$ radiation. The EMM-31 material may have at least seven, at least eight, at least nine, or ten XRD peaks selected from Table 1 or Table 1A.

The EMM-31 material (where part or all of the SDA is removed) may have a framework defined by the connectivities in Table 2 for the tetrahedral (T) atoms in the unit cell, where the tetrahedral (T) atoms are connected by bridging atoms. The connectivities can be calculated by the computer algorithm zeoTsites, a Fortran code for topological and crystallographic tetrahedral sites analysis in zeolites and zeotypes. See e.g., G. Sastre, J. D. Gale, *Microporous and Mesoporous Materials* 2001, 43, pages 27-40. The tetrahedral atoms may include one or more elements selected from B, Al, Fe, Ga, Si, Ge, Sn, Ti, and Zr, or a mixture thereof. For example, the tetrahedral atoms may be selected from B, Al, or Si, or a mixture thereof. For example, the tetrahedral atoms may comprise or be Si or Al. The bridging atoms may be selected from O, N, and C, or a mixture thereof. The bridging atoms may be oxygen atoms (e.g., at least 50%, at least 60%, at least 70%, at least 80%, at least 90%, or at least 95% of the bridging atoms may be oxygen). The bridging atom C may be incorporated from the various sources used to make the zeolite, e.g., the silica source. The bridging atom N may be incorporated into the zeolite after the SDA has been removed.

In one or more aspects, the EMM-31 material (where part or all of the SDA has been removed by thermal treatment or other treatments) may have a micropore volume of 0.10 to 0.25 cc/g, e.g., 0.22 cc/g.

For example, the material (where part or all of the SDA has been removed) may have XRD peaks selected from:

| degree 2-theta (±0.2) | relative intensity [100 × I/(Io)] |
|---|---|
| 6.39 | 60-100 |
| 7.78 | 60-80 |
| 8.22 | 20-40 |
| 8.82 | 20-40 |
| 19.40 | 60-100 |
| 23.13 | 60-90 | and a micropore volume of 0.10 to 0.25 cc/g.

In one or more aspects, the EMM-31 material (where part or all of the SDA is removed) may have a C-centered unit cell a-parameter of 17.9±0.5 Å, b-parameter of 21.4±0.5 Å, and c-parameter of 20.0±0.5 Å.

For example, the material may have XRD peaks selected from:

| degree 2-theta (±0.2) | relative intensity [100 × I/(Io)] |
|---|---|
| 6.39 | 60-100 |
| 7.78 | 60-80 |
| 8.22 | 20-40 |
| 8.82 | 20-40 |
| 19.40 | 60-100 |
| 23.13 | 60-90 | and a C-centered unit cell a-parameter of 17.9±0.5 Å, b-parameter of 21.4±0.5 Å, and c-parameter of 20.0±0.5 Å.

In one or more aspects, the EMM-31 material (where part or all of the SDA is removed) may adsorb at least 60 mg (miligrams) of n-hexane per g (gram) EMM-31 material (e.g., 60 to 150 mg/g of n-hexane) upon contact with a fluid containing n-hexane component. The material may also be suitable for adsorbing at least 40 mg/g of mesitylene (e.g., 40 to 100 mg/g of mesitylene). For example, the material may adsorb 70 to 140, 80 to 120, 90 to 110, or 100 mg/g of n-hexane. The material may adsorb 40 to 80, 50 to 70, or 60 mg/g of mesitylene.

For example, the material (where part or all of the SDA) may have XRD peaks selected from:

| degree 2-theta (±0.2) | relative intensity [100 × I/(Io)] |
|---|---|
| 6.39 | 60-100 |
| 7.78 | 60-80 |
| 8.22 | 20-40 |
| 8.82 | 20-40 |
| 19.40 | 60-100 |
| 23.13 | 60-90 | and may adsorb at least 60 mg/g n-hexane (e.g., 60 to 150 mg/g of n-hexane or 100 mg/g of n-hexane) or at least 40 mg/g mesitylene (e.g., 40 to 100 mg/g of mesitylene or 60 mg/g of mesitylene).

For example, the material (where part or all of the SDA is removed) may have XRD peaks selected from:

| degree 2-theta (±0.2) | relative intensity [100 × I/(Io)] |
|---|---|
| 6.39 | 60-100 |
| 7.78 | 60-80 |
| 8.22 | 20-40 |
| 8.82 | 20-40 |
| 19.40 | 60-100 |
| 23.13 | 60-90 | and (i) a micropore volume of 0.10 to 0.25 cc/g; (ii) a C-centered unit cell a-parameter of 17.9±0.5 Å, b-parameter of 21.4±0.5 Å, and c-parameter of 20.0±0.5 Å; and/or (iii) adsorb at least 60 mg/g n-hexane (e.g., 60 to 150 mg/g of n-hexane) or at least 40 mg/g mesitylene (e.g., 40 to 100 mg/g of mesitylene).

In one or more aspects, the EMM-31 material (where part or all of the SDA is removed) may be optionally represented by Formula I:

$$(v)X_2O_3:YO_2 \quad \text{(Formula I)},$$

wherein $0.0005 \leq v \leq 0.1$, X is a trivalent element, and Y is a tetravalent element. X may be selected from B, Al, Fe, and Ga, or a mixture thereof. For example, X may comprise or be Al or X may comprise or be B. Y may be selected from Si, Ge, Sn, Ti, and Zr, or a mixture thereof. For example, Y may comprise or be Si. The oxygens in Formula I may be replaced by carbon atoms (e.g., in the form of $CH_2$), which can come from sources of the reagents used to prepare the as-made EMM-31. The oxygens in Formula I can also be replaced by nitrogen atoms, e.g., after the SDA has been removed. Formula I can represent the framework of a typical EMM-31 material where part or all of the SDA has been removed, and is not meant to be the sole representation of an EMM-31 material. The EMM-31 material may contain SDA and/or impurities after appropriate treatments to remove the SDA and impurities, which are not accounted for in Formula I. Further, Formula I does not include the protons and charge compensating ions that may be present in the EMM-31 material.

The variable v represents the molar ratio relationship of $X_2O_3$ in Formula I. For example, when v is 0.0005, the molar ratio of Y to X is 1000 (e.g., the molar ratio of Si/B or Si/Al is 1000). When v is 0.1, the molar ratio of Y to X is 5 (e.g., the molar ratio of Si/B or Si/Al is 5). The molar ratio of Y to X may be 5 to 40 or 5 to 25 when X is B (e.g., the molar ratio of Si/B is 5 to 40 or 5 to 25). The molar ratio of Y to X may be 50 to 1000, 100 to 1000, 200 to 1000, 300 to 1000, 400 to 1000, or 500 to 1000 when X is Al (e.g., the molar ratio of Si/Al is 100 to 1000 or 500 to 1000).

The as-made (e.g., without treatment to remove the SDA) EMM-31 material may have at least six XRD peaks in degree 2-theta selected from Table 3:

TABLE 3

| degree 2-theta (±0.2) | relative intensity [100 × I/(Io)] |
|---|---|
| 6.34 | 20-60 |
| 7.75 | 10-30 |
| 8.25 | 20-60 |
| 8.71 | 20-40 |
| 9.32 | 1-20 |
| 15.47 | 1-20 |
| 19.37 | 40-80 |
| 21.40 | 40-70 |
| 22.92 | 60-100 |
| 23.51 | 20-50 |

The as-made (e.g., without treatment to remove the SDA) EMM-31 material may have at least six XRD peaks with the degree 2-theta and d-spacing values selected from Table 3A, wherein the d-spacing values have a deviation determined based on the corresponding deviation±0.20 degree 2-theta when converted to the corresponding values for d-spacing using Bragg's law:

TABLE 3A

| degrees 2-theta (±0.2) | d-spacing (Å) | relative intensity [100 × I/(Io)] |
|---|---|---|
| 6.34 | 13.92 | 20-60 |
| 7.75 | 11.39 | 10-30 |
| 8.25 | 10.71 | 20-60 |
| 8.71 | 10.14 | 20-40 |
| 9.32 | 9.48 | 1-20 |
| 15.47 | 5.73 | 1-20 |
| 19.37 | 4.58 | 40-80 |
| 21.40 | 4.15 | 40-70 |
| 22.92 | 3.88 | 60-100 |
| 23.51 | 3.78 | 20-50 |

The as-made EMM-31 material may have at least seven, at least eight, at least nine, or ten XRD peaks selected from Table 3 or Table 3A.

In one or more aspects, the as-made EMM-31 material may be described as having a C-centered unit cell a-parameter of 17.9±0.5 Å, b-parameter of 21.3±0.5 Å, and c-parameter of 20.2±0.5 Å. For example, the as-made material may have at least six XRD peaks selected from Table 3 or Table 3A and a C-centered unit cell a-parameter of 17.9±0.5 Å, b-parameter of 21.3±0.5 Å, and c-parameter of 20.2±0.5 Å. For example, the as-made EMM-31 material may have at least six, at least seven, at least eight, at least nine, or ten XRD peaks selected from Table 3 or Table 3A; and a C-centered unit cell a-parameter of 17.9±0.5 Å, b-parameter of 21.3±0.5 Å, and c-parameter of 20.2±0.5 Å.

In one or more aspects, the as-made EMM-31 material may optionally be represented by Formula II:

$$(n)G:(v)X_2O_3:YO_2 \quad \text{(Formula II)},$$

wherein 0.01≤n≤0.3, 0.0005≤v≤0.1, G is an organic structure directing agent, X is a trivalent element, and Y is a tetravalent element. X may be selected from B, Al, Fe, and Ga, or a mixture thereof. For example, X may comprise or be Al or B. Y may be selected from Si, Ge, Sn, Ti and Zr, or a mixture thereof. For example, Y may comprise or be Si. Formula II can represent the framework of a typical as-made EMM-31 material with SDA, and is not meant to be the sole representation of such material. The as-made EMM-31 material may contain impurities that are not represented by Formula II. Further, Formula II does not include the protons and charge compensating ions that may be present in the as-made EMM-31 material. Similar to Formula I, the oxygens in Formula II may be replaced by carbon atoms (e.g., in the form of $CH_2$), which can come from sources of the reagents used to prepare the as-made EMM-31.

The variable v represents the molar relationship of $X_2O_3$ in Formula II. The values for variable v in Formula II are the same as those described herein for Formula I. The variable n represents the molar relationship of SDA (G) in Formula II. For example, when n is 0.01, the molar ratio of G to Y is 0.01. When n is 0.3, the molar ratio of G to Y is 0.3. The molar ratio of G to Y may be 0.1 to 0.2 or 0.1 or 0.15.

The process used to prepare the as-made EMM-31 materials may be described as follows:
(i) mixing a composition comprising a source of hydroxide ions, a source of an oxide of a tetravalent element Y, a source of a trivalent element X, and a structure directing agent (G) comprising a bispyrrolidinium dication;
(ii) heating the mixed composition; and
(iii) isolating the crystals of EMM-31 material.

Stated otherwise, the as-made EMM-31 material may be prepared by a process that includes isolating crystals of EMM-31 materials from a composition. The process may further include heating the composition. The process further includes mixing the composition that includes a structure directing agent (G), e.g., a bispyrrolidinium dication. Alternatively, EMM-31 may be made without using an SDA. The composition of the source of hydroxide ions and the source of the oxide of a tetravalent element Y may also include a source of a trivalent element X. For example, the composition used to prepare EMM-31 may include a source of hydroxide ions, a source of an oxide of a tetravalent element Y, a source of a trivalent element X, and an SDA (G) such as a bispyrrolidinium dication. The composition may have a molar ratio of $YO_2$ to $H_3XO_3$ (e.g., $H_3BO_3$) or $YO_2$ to $X_2O_3$ (e.g., $Al_2O_3$) of 5 to 30 (e.g., 5 to 15). The composition may also have a molar ratio of $H_2O$ to $YO_2$ of 1 to 50 (e.g., 10 to 40). The composition may also have a molar ratio of $OH^-$ to $YO_2$ of 0.05 to 0.6 (e.g., 0.15 to 0.5). The composition may have a molar ratio of G to $YO_2$ of 0.03 to 0.3 (e.g., 0.05 to 0.3, or 0.05 to 0.2). The trivalent element X used in the synthesis may be B resulting in the as-made material being a borosilicate.

Carbon in the form of $CH_2$ may be present in the various sources of reagents used to prepare EMM-31, e.g., tetravalent element source (silica source), and incorporated into the EMM-31 framework as bridging atoms. Nitrogen atoms may be incorporated into the framework of the EMM-31 material after the SDA has been removed as bridging atoms.

Optionally, the as-made EMM-31 material may be prepared by mixing a trivalent element X source with a hydroxide solution of SDA, and then subsequently adding a tetravalent Y source to the mixture to form a base mixture of the components. Seeds of an EMM-31 material may be added to the base mixture. In one or more aspects, the mixture after solvent adjustment (e.g., where the desired water to silica ratio is achieved) is mixed by a mechanical process such as stirring or high shear blending to assure suitable homogenization of the base mixture, for example, using dual asymmetric centrifugal mixing (e.g., a FlackTek speedmixer) with a mixing speed of 1000 to 3000 rpm (e.g., 2000 rpm). Depending on the nature of the reagents in the base mixture, the amount of solvent (e.g., water from the hydroxide solution, and optionally methanol and ethanol from the hydrolysis of silica sources) of the base mixture may be removed such that a desired solvent to $YO_2$ molar ratio is achieved for the resulting mixture. Suitable methods for reducing the solvent content may include evaporation under a static or flowing atmosphere such as ambient air, dry nitrogen, dry air, or by spray drying or freeze drying. Water may be added to the resulting mixture to achieve a desired $H_2O/YO_2$ molar ratio when too much water is removed during the solvent removal process.

The mixed mixture is then subject to crystallization conditions suitable for the EMM-31 material to form. Crystallization of an EMM-31 material may be carried out under static or stirred conditions in a suitable reactor vessel, such as for example, polypropylene jars or Teflon lined or stainless steel (SS) autoclaves placed in a convection oven maintained at a temperature of about 100 to about 200° C. for a period of time sufficient for crystallization to occur, e.g., from about 1 day to about 30 days (e.g., 1 day to 14 days, or 1 day to 7 days). Unless indicated otherwise herein, the temperature measured is the temperature of the surrounding environment of the material being heated, for example the temperature of the atmosphere in which the material is heated. Thereafter, the solid crystals of the as-made EMM-31 material are separated from the liquid (e.g., by filtration or centrifugation) and recovered.

Examples of sources of the tetravalent element Y may be selected from colloidal suspensions of silica, precipitated silica, fumed silica, alkali metal silicates, tetraalkyl orthosilicates (e.g., tetraethyl orthosilicate, tetramethyl orthosilicate, etc), and germanium oxide, or a mixture thereof. Other examples of sources of silica may include LUDOX® (e.g., LUDOX® LS-30, LUDOX® AS-40) colloidal silica, SIPERNAT® precipitated silica, CARBOSPERSE™ fumed silica suspension, or a mixture thereof.

In one or more aspects, the trivalent element X may be boron or aluminum. Suitable sources of aluminum may be selected from hydrated alumina, aluminum hydroxide, alkali metal aluminates, aluminum alkoxides, and water-soluble aluminum salts, such as aluminum nitrate, or a mixture thereof. Suitable sources of boron may be selected from boric acid, sodium tetraborate, and potassium tetraborate, or a mixture thereof. For example, the boron source may be boric acid.

In one or more aspects, the EMM-31 material may be prepared using boric acid as the source of the trivalent element. The as-made EMM-31 comprising boron may be thermally-treated (e.g., calcined) to remove part or all of the SDA. The thermally-treated EMM-31 material comprising boron may be described as having a 0.10 to 0.25 cc/g (e.g., 0.22 cc/g) micropore volume and/or 60 to 90 m²/g (e.g., 75 m²/g) external surface area. Optionally, the material (where part or all of the SDA has been removed) having X is B and Y is Si may be contacted with an Al source under conditions sufficient to exchange the B in the framework with Al. For example, the thermally-treated EMM-31 comprising boron may be converted to an aluminosilicate by heating the thermally-treated EMM-31 material comprising boron with a solution of $Al_2(SO_4)_3$ (e.g., in a sealed autoclave in a convection oven for overnight maintained at 100° C. or at boiling temperature in an open system). The aluminum treated EMM-31 may then be recovered by filtration and washed with deionized water. The aluminum treated EMM-31 may have an alpha value (which is described herein, vide infra) of about 140.

Part or all of the SDA used during the synthesis of an as-made EMM-31 material may be removed by thermal treatment, ozone treatment, or other treatments to form the EMM-31 material that is substantially free of the SDA (e.g., greater than 50%, 60%, 70%, 80%, 90%, 95% or 99% (based on weight) free of SDA). Removal of SDA may be carried out using thermal treatment (e.g., calcination) in which the as-made EMM-31 material is heated in an atmosphere selected from air, nitrogen, or a mixture thereof at a temperature sufficient to remove part or all of the SDA. While subatmospheric pressure may be employed for the thermal treatment, atmospheric pressure is desired for reasons of convenience. The thermal treatment may be performed at a temperature up to 700° C., e.g., from 400° C. to 700° C. The thermal treatment (e.g., calcination) may be carried out in a box furnace in dry air, which has been exposed to a drying tube containing drying agents that remove water from the air. The heating may be carried out for 1 day to 14 days at 400° C. to 700° C. (e.g., 540° C.). The heating may first be carried out under a nitrogen atmosphere up to 400° C. and then the atmosphere may be switched to air at 400° C. to 600° C.

The as-made EMM-31 material includes a structure directing agent, e.g., a bispyrrolidinium dication. Alternative methods of synthesizing the EMM-31 material may be carried out without the use of an SDA. Suitable sources of the structure directing agents may be selected from the hydroxides and/or salts of the relevant diquaternary ammonium compounds.

In one or more aspects, a structure directing agent useful for synthesizing a zeolite, for example an as-made EMM-31 material, may be Compound E having the following structure:

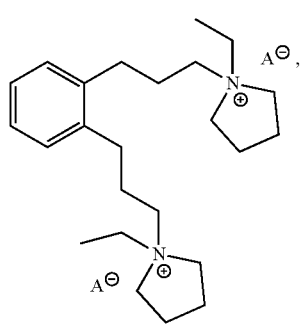
(Compound E)

wherein A is an ion.
For example, A may be tosylate, OH or halide, such as I or Br. For example, both A ions may be OH.

The process of preparing Compound E may comprise:
(i) converting Compound 1.

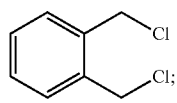
Compound 1 to Compound 2R:

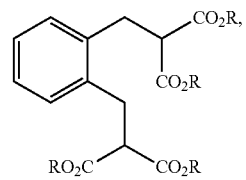
Compound 2R wherein R is alkyl (e.g., $C_{1-10}$ alkyl);
(ii) converting Compound 2R to Compound 3:

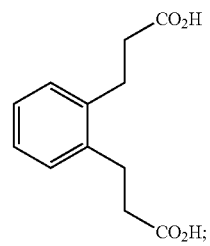
Compound 3

(iii) converting Compound 3 to Compound 4R:

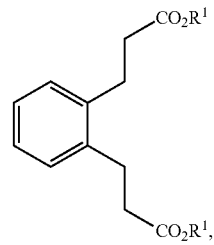
Compound 4R wherein $R^1$ is alkyl (e.g., $C_{1-10}$ alkyl);
(iv) converting Compound 4R to Compound 5:

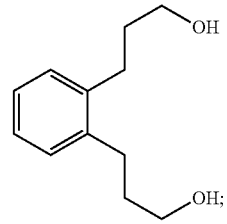
Compound 5

(v) converting Compound 5 to Compound 6:

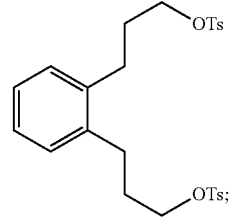
Compound 6

(vi) converting Compound 6 to Compound 7:

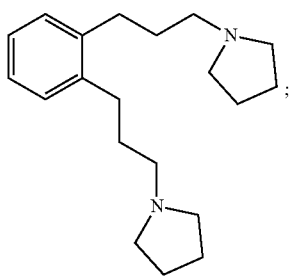

Compound 7

(vii) converting Compound 7 to Compound E.

Compound 2R may be prepared by converting Compound 1 to Compound 2R. For example, Compound 1 may be reacted with dialkyl malonate (e.g., diethyl malonate) and a base. Suitable bases may be hydride bases, such as sodium hydride. The amount of hydride used may be 2 to 5 molar equivalents (e.g., 2.5 or 3 molar equivalents) of the hydride based on 1 molar equivalent of Compound 1. The amount of dialkyl malonate (e.g., diethyl malonate) used may be 2 to 5 molar equivalents (e.g., 3 molar equivalents) of dialkyl malonate based on 1 molar equivalent of Compound 1. The conversion of Compound 1 to Compound 2R may be carried out in the presence of a solvent, such as a polar solvent (e.g., dimethylformamide).

Compound 3 may be prepared by converting Compound 2R to Compound 3. The conversion of Compound 2R to Compound 3 may comprise reacting Compound 2R with a base and then an acid. Suitable bases may comprise or be hydroxide bases, e.g., sodium hydroxide. The acid may comprise or be sulfuric acid (e.g., concentrated sulfuric acid).

Compound 4R may be prepared by converting Compound 3 to Compound 4R. For example, Compound 3 may be reacted with ethanol in the presence an acid. The acid may comprise or be sulfuric acid (e.g., concentrated sulfuric acid). The conversion may be carried out at the reflux temperature of the mixture of Compound 3, ethanol, and the acid for a time sufficient for Compound 3 to be converted Compound 4R. For example, the conversion may be refluxed for about 1 hour to 24 hours (e.g., 12 to 18 or 14 to 16 hours).

Compound 5 may be prepared by converting Compound 4R to Compound 5. The conversion may include reacting Compound 4R with a reducing agent in the presence of a solvent. The reducing agent may comprise or be lithium aluminum hydride. Suitable solvents may comprise or be an ether, e.g., the solvent may comprise or be tetrahydrofuran, diethylether or a mixture thereof. The amount of the reducing agent (e.g., LiAlH$_4$) used may be 1 to 2 molar equivalents (e.g., 1.5 or 1.6 molar equivalents) of 1 molar equivalent of Compound 4R.

Compound 6 may be prepared by converting Compound 5 to Compound 6. For example, Compound 5 may be reacted with a tosylate source and a base. A suitable tosylate source may comprise or be tosyl chloride. The base may comprise or be pyridine. A base such as pyridine may also function as a solvent in the reaction mixture. Alternatively, the reaction may be carried out in the presence of polar solvent such as a halogenated solvent e.g., chloroform. The amount of the tosylate source (e.g., tosyl chloride) used may be 1 to 3 molar equivalents (e.g., 2 molar equivalents) based on 1 molar equivalent of Compound 5.

Compound 7 may be prepared by converting Compound 6 to Compound 7. The conversion may comprise reacting Compound 6 with pyrrolidine in the presence of a solvent. The solvent may comprise or be an aprotic solvent, such as acetonitrile, chloroform, or a mixture thereof. The amount of pyrrolidine used may be 3 to 10 or 5 to 10 molar equivalents (e.g., 7 molar equivalents) based on 1 molar equivalent of Compound 6.

The process of preparing Compound E may comprise converting Compound 7 to Compound E. For example, the process may comprise reacting Compound 7 with a halo alkane (e.g., an iodide or bromide source) in the presence of a solvent. The iodide source may comprise or be iodoethane. The solvent may comprise or be an aprotic solvent (e.g., acetonitrile). The amount of iodoethane used may be 3 to 10 or 5 to 10 molar equivalents (e.g., 7 molar equivalents) based on 1 molar equivalent of Compound 7.

The anions of Compound E may be converted to other anions. For example, the anion tosylate or iodide may be converted to the hydroxide anion. For example, Compound E with iodine as the anion may be treated with a hydroxide resin (e.g., 400 mL Dowex® SBR LC NG (OH) resin or Dowex® Monosphere™ 550A UPW OH resin). The resin may be washed with water. A sample of Compound E (anion is iodine), resin and water may be sealed and rolled at 10 revolutions per minute (RPM) for 1 hour. The sample may then be filtered, and the resin may washed with water (e.g., about 800 mL water so the final pH of the last drop is ~11).

In one or more aspects, Compound 5 may alternatively be prepared as follows:

(i) converting 1,2-diiodobenzene to Compound 1a:

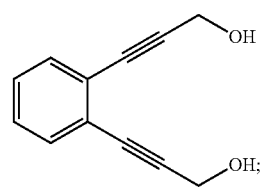

Compound 1a and (ii) converting Compound 1a to Compound 5.

Compound 1a may be prepared according to the procedures reported in *J. Phys. Org. Chem.*, 2011, 24, 969-975, the content of which is incorporated herein by reference in its entirety. The conversion of 1,2-diiodobenzene to Compound 1a may be carried out in the presence of propargyl alcohol, a palladium catalyst, CuI, and a base. The palladium catalyst may comprise or be bis(triphenylphosphine)palladium dichloride. The base may comprise or be an amine base, such as diethylamine or trimethylamine. The conversion may be carried out in a solvent, such as an ether solvent (e.g., the ether solvent may comprise or be tetrahydrofuran). The amount of the palladium catalyst used may be 0.05 to 0.2 molar equivalent (e.g., 0.09 or 0.1 molar equivalent) based on 1 molar equivalent of 1,2-diiodobenzene. The amount of CuI used may be 0.01 to 0.1 molar equivalent (e.g., 0.05 or 0.06 molar equivalent) based on 1 molar equivalent of 1,2-diiodobenzene. The amount of propargyl alcohol used may be 2 to 6 molar equivalents (e.g., 4 molar equivalents) based on 1 molar equivalent of 1,2-diiodobenzene.

The process of preparing Compound 5 may comprise converting Compound 1a to Compound 5. For example, Compound 1a may be reacted with palladium and hydrogen. The palladium may be or comprise palladium on charcoal (e.g., 10% palladium on charcoal). The hydrogen may be or comprise hydrogen gas (e.g., 900 psi of hydrogen gas). The reaction may be carried out in the presence of a polar solvent (e.g., methanol), an ether solvent (e.g., tetrahydrofuran), or a mixture thereof (e.g., 80:20 THF:MeOH).

Compound 5 may be converted to Compound 6 as described above and in the Examples.

In one or more aspects, Compound E may alternatively be prepared by treating Compound 6 with N-ethylpyrrolidine to generate Compound E without going through the intermediate process of preparing Compound 7. The conversion may be carried out in the presence of a solvent, such as an aprotic solvent, e.g., acetonitrile. The amount of N-ethylpyrrolidine used may be 2 to 5 molar equivalents (e.g., 2 to 4 or 3 molar equivalents) based on 1 molar equivalent of Compound 6.

In one or more aspects, Compound E may alternatively be prepared by a process comprising:
 (i) converting 1,2-diiodobenzene to Compound 1a;
 (ii) converting Compound 1a to Compound 5;
 (iii) converting Compound 5 to Compound 6; and
 (iv) converting Compound 6 to Compound E.

The anions of Compound E may be converted to other anions. For example, the anion tosylate or iodide may be converted to the hydroxide anion by methods described herein or standard methods as described in "Ion Exchange Training Manual" George P. Simon, Van Nostrand Reinhold NY 1991.

General Features

EMM-31 materials (where part or all of the SDA is removed) may be combined with a hydrogenating component. The hydrogenating component may be selected from molybdenum, tungsten, rhenium, nickel, cobalt, chromium, manganese, or a noble metal, such as platinum or palladium where a hydrogenation-dehydrogenation function is to be performed. Such hydrogenating components may be incorporated into the composition by way of one or more of the following processes: cocrystallizing; exchanging into the composition to the extent a Group IIIA element, e.g., aluminum, is in the structure; impregnating therein or physically admixing therewith. For example, such hydrogenating components may be impregnated into the EMM-31 material. In the case of platinum, the EMM-31 materials may be impregnated with a solution containing a platinum metal-containing ion. Suitable platinum compounds for impregnating may be selected from chloroplatinic acid, platinous chloride, compounds containing a platinum amine complex, or a mixture thereof.

EMM-31 materials (where part or all of the SDA is removed), when employed either as an adsorbent or as a catalyst, may be dehydrated, at least partially. Such dehydration may be accomplished by heating the material in a surrounding atmosphere at a temperature in the range of 200 to 370° C., the atmosphere may be selected from air, nitrogen, or a mixture thereof, and at atmospheric, subatmospheric or superatmospheric pressures for between 30 minutes and 48 hours. Dehydration may also be performed at room temperature by placing the EMM-31 materials in a vacuum; however, a longer period of time is required to obtain a sufficient amount of dehydration.

EMM-31 materials (where part or all of the SDA is removed) may be used as an adsorbent or in an aluminosilicate form, as a catalyst to catalyze a wide variety of organic compound conversion processes. Examples of chemical conversion processes, which are effectively catalyzed by the modified EMM-31 materials described herein, either alone or in combination with one or more other catalytically active substances (including other crystalline catalysts), include those requiring a catalyst with acid activity. Examples of organic conversion processes, which may be catalyzed by the modified EMM-31 materials described herein include cracking, hydrocracking, disproportionation, alkylation, oligomerization, and isomerization.

EMM-31 materials (where part or all of the SDA is removed) may be incorporated with another material resistant to the temperatures and other conditions employed in organic conversion processes. Such resistant materials may be selected from active materials, inactive materials, synthetic zeolites, naturally occurring zeolites, inorganic materials or a mixture thereof. Examples of such resistant materials may be selected from clays, silica, metal oxides such as alumina, or a mixture thereof. The inorganic material may be either naturally occurring, or in the form of gelatinous precipitates or gels, including mixtures of silica and metal oxides. Use of a resistant material in conjunction with an EMM-31 material, i.e., combined therewith or present during synthesis of the as-made EMM-31 crystal, which crystal is active, tends to change the conversion and/or selectivity of the catalyst in certain organic conversion processes. Inactive resistant materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said inactive resistant materials, i.e., clays, oxides, etc., function as binders for the catalyst. A catalyst having good crush strength can be beneficial because in commercial use, it is desirable to prevent the catalyst from breaking down into powder-like materials.

Naturally occurring clays which may be composited with EMM-31 materials include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays may be used in the raw state as originally mined or initially subjected to calcination, acid treatment or chemical modification. Binders useful for compositing with EMM-31 materials also include inorganic oxides selected from silica, zirconia, titania, magnesia, beryllia, alumina, or a mixture thereof.

EMM-31 materials (where part or all of the SDA is removed) may be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

The relative proportions of EMM-31 material and inorganic oxide matrix may vary widely, with the EMM-31 material content ranging from about 1 to about 90 percent by weight, of the composite or, when the composite is prepared in the form of beads, in the range of about 2 to about 80 weight percent of the composite.

As used herein, and unless otherwise specified, a numeric value or range of values may deviate to an extent deemed reasonable to one of ordinary skill in the relevant art. It is well known that instrument variation and other factors can affect the numerical values. Such deviation, unless otherwise specified, may be plus or minus 2%, 5%, 10%, 15%, 20%, 25%, or 30% of the numeric value or range of values indicated.

The EMM-31 materials described herein may be at least 50%, at least 60%, at least 70%, at least 80%, at least 90%, at least 95%, at least 97%, or at least 99% (e.g., 99.5% or 99.9%) by weight pure EMM-31 material, based on the total weight of the composition, by quantification using XRD or NMR spectroscopy (e.g., by measuring the area or the relative intensity of the relevant peaks), or by other known methods appropriate for such determination. The remainder of the material is non-EMM-31 material, which may be structure directing agent, amorphous material, other impurities, or a mixture thereof.

The EMM-31 material described herein is substantially crystalline. As used herein, the term "crystalline" refers to a crystalline solid form of a material, including, but not limited to, a single-component or multiple-component crystal form, e.g., including solvates, hydrates, and a co-crystal. Crystalline can mean having a regularly repeating and/or ordered arrangement of atoms, and possessing a distinguishable crystal lattice. For example, crystalline EMM-31 can have different water or solvent content. The different crystalline lattices can be identified by solid state characterization methods such as by XRD (e.g., powder XRD). Other characterization methods known to a person of ordinary skill in the relevant art can further help identify the crystalline form as well as help determine stability and solvent/water content.

As used herein, the term "substantially crystalline" means a majority (greater than 50%) of the weight of a sample of a solid material described is crystalline and the remainder of the sample is a non-crystalline form. In one or more aspects, a substantially crystalline sample has at least 95% crystallinity (e.g., 5% of the non-crystalline form), at least 96% crystallinity (e.g., 4% of the non-crystalline form), at least 97% crystallinity (e.g., 3% of the non-crystalline form), at least 98% crystallinity (e.g., about 2% of the non-crystalline form), at least 99% crystallinity (e.g., 1% of the non-crystalline form), and 100% crystallinity (e.g., 0% of the non-crystalline form).

As used herein, the term "alpha value" refers to the catalytic activity of a material (e.g., the EMM-31 material described herein) measured by the ratio of the rate constant of a test sample for cracking normal hexane to the rate constant of a standard reference catalyst, which is an amorphous silica/alumina. See e.g., P. B. Weisz and J. N. Miale, *J. Catalysis*, 4 (1965) 527-529; and J. N. Miale, N. Y. Chen, and P. B. Weisz, *J. Catalysis*, 6 (1966) 278-287. For example, an alpha value of 1 means that the test sample and the reference standard have about the same activity.

The micropore volume of the modified EMM-31 materials described herein can be determined using methods known in the relevant art. For example, the materials can be measured with nitrogen physisorption, and the data can be analyzed by the t-plot method described in Lippens, B. C. et al., "Studies on pore system in catalysts: V. The t method", *J. Catal.*, 4, 319 (1965), which describes micropore volume method and is incorporated herein by reference.

As used herein, the term "alkyl" refers to a saturated hydrocarbon group that may be straight-chained or branched. The term "$C_{n-m}$ alkyl", refers to an alkyl group having n to m carbon atoms. An alkyl group corresponds to an alkane with one C—H bond replaced by the point of attachment of the alkyl group to the remainder of the compound. The alkyl group may contain from 1 to 6 carbon atoms, from 1 to 4 carbon atoms, from 1 to 3 carbon atoms, or 1 to 2 carbon atoms. Examples of alkyl moieties include groups such as methyl, ethyl, n-propyl, isopropyl, n-butyl, tert-butyl, isobutyl, sec-butyl, and the like.

Figure 2:
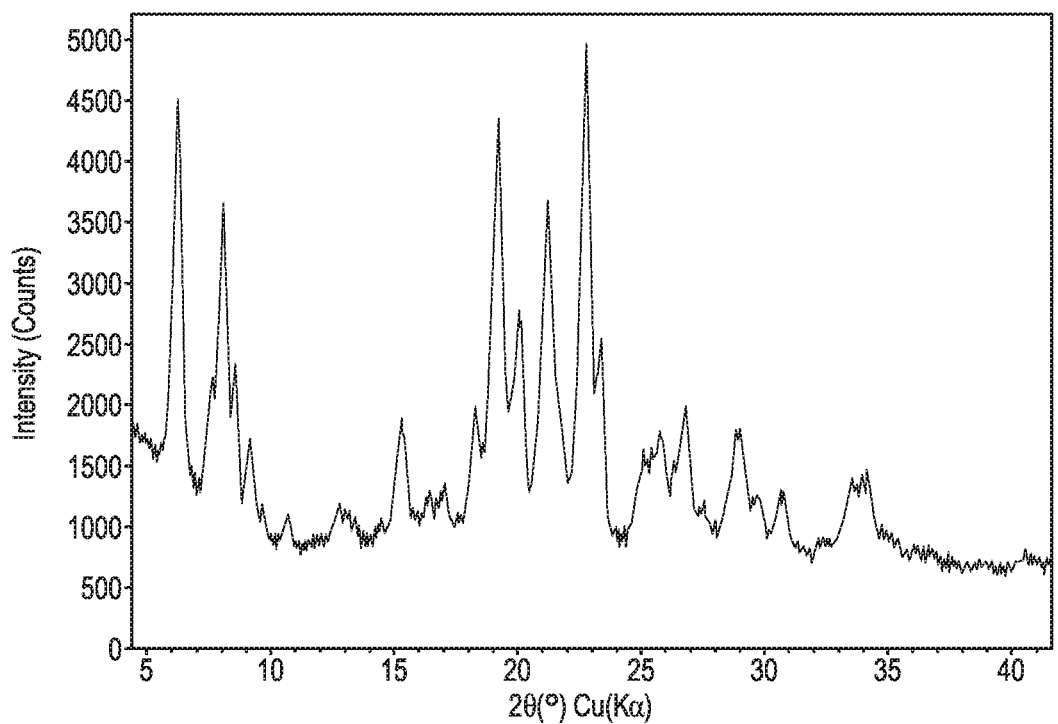
FIG. 2 shows a powder XRD pattern of an as-made EMM-31 material using a potassium-containing reagent.

The X-ray diffraction data reported herein were collected with a Bruker D4 Endeavor instrument in continuous mode using Cu Kα radiation with a step size of 0.01796° with the VÅNTEC-1 gaseous detector with 50 mm×16 mm active area. FIGS. 1 and 2 were collected at an effective count time of 278 sec/step and FIG. 3 at 347.5 sec/step. The interplanar spacings, d-spacings, were calculated in Angstrom units, and the relative intensities of the lines, $I/I_o$ is the ratio of the peak intensity to that of the intensity of the strongest line, above background. The intensities are uncorrected for Lorentz and polarization effects. The location of the diffraction peaks in 2-theta, and the relative peak area intensities of the lines, I/I(o), where Io is the intensity of the strongest line, above background, were determined with the MDI Jade peak search algorithm. It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

Aspects of the disclosure are described in greater detail by way of specific examples. The following examples are offered for illustrative purposes, and are not intended to limit the disclosure in any manner. Those of skill in the relevant art will readily recognize a variety of parameters can be changed or modified to yield essentially the same results.

EXAMPLES

Example 1: Synthesis of Compound E

Compound E where the anion is iodide or hydroxide was synthesized according to Scheme 1.

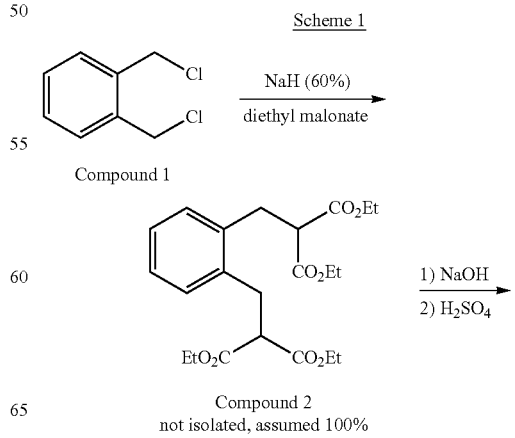

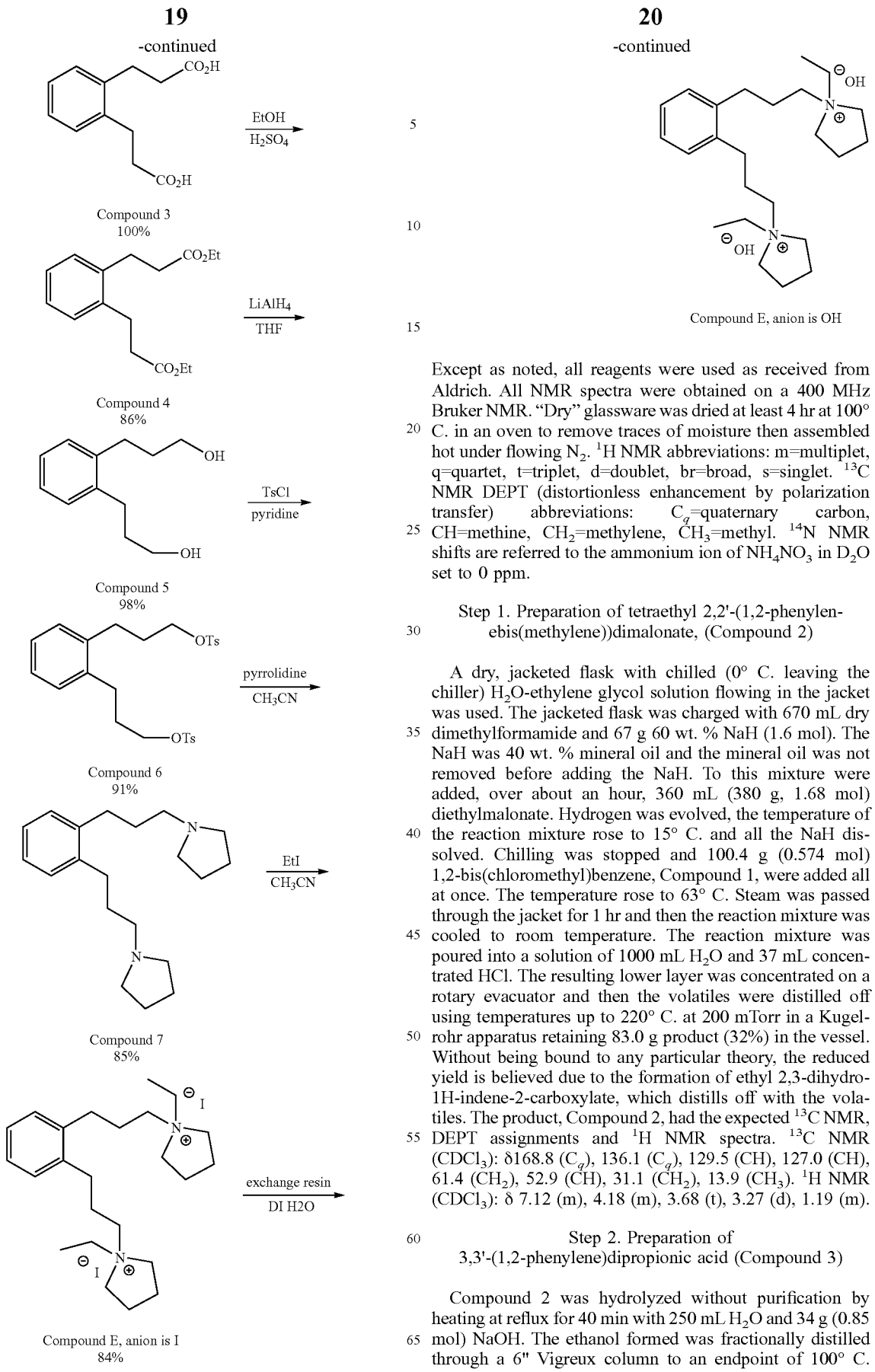

Except as noted, all reagents were used as received from Aldrich. All NMR spectra were obtained on a 400 MHz Bruker NMR. "Dry" glassware was dried at least 4 hr at 100° C. in an oven to remove traces of moisture then assembled hot under flowing $N_2$. $^1$H NMR abbreviations: m=multiplet, q=quartet, t=triplet, d=doublet, br=broad, s=singlet. $^{13}$C NMR DEPT (distortionless enhancement by polarization transfer) abbreviations: $C_q$=quaternary carbon, CH=methine, $CH_2$=methylene, $CH_3$=methyl. $^{14}$N NMR shifts are referred to the ammonium ion of $NH_4NO_3$ in $D_2O$ set to 0 ppm.

Step 1. Preparation of tetraethyl 2,2'-(1,2-phenylenebis(methylene))dimalonate, (Compound 2)

A dry, jacketed flask with chilled (0° C. leaving the chiller) $H_2O$-ethylene glycol solution flowing in the jacket was used. The jacketed flask was charged with 670 mL dry dimethylformamide and 67 g 60 wt. % NaH (1.6 mol). The NaH was 40 wt. % mineral oil and the mineral oil was not removed before adding the NaH. To this mixture were added, over about an hour, 360 mL (380 g, 1.68 mol) diethylmalonate. Hydrogen was evolved, the temperature of the reaction mixture rose to 15° C. and all the NaH dissolved. Chilling was stopped and 100.4 g (0.574 mol) 1,2-bis(chloromethyl)benzene, Compound 1, were added all at once. The temperature rose to 63° C. Steam was passed through the jacket for 1 hr and then the reaction mixture was cooled to room temperature. The reaction mixture was poured into a solution of 1000 mL $H_2O$ and 37 mL concentrated HCl. The resulting lower layer was concentrated on a rotary evacuator and then the volatiles were distilled off using temperatures up to 220° C. at 200 mTorr in a Kugelrohr apparatus retaining 83.0 g product (32%) in the vessel. Without being bound to any particular theory, the reduced yield is believed due to the formation of ethyl 2,3-dihydro-1H-indene-2-carboxylate, which distills off with the volatiles. The product, Compound 2, had the expected $^{13}$C NMR, DEPT assignments and $^1$H NMR spectra. $^{13}$C NMR (CDCl$_3$): δ168.8 ($C_q$), 136.1 ($C_q$), 129.5 (CH), 127.0 (CH), 61.4 ($CH_2$), 52.9 (CH), 31.1 ($CH_2$), 13.9 ($CH_3$). $^1$H NMR (CDCl$_3$): δ 7.12 (m), 4.18 (m), 3.68 (t), 3.27 (d), 1.19 (m).

Step 2. Preparation of 3,3'-(1,2-phenylene)dipropionic acid (Compound 3)

Compound 2 was hydrolyzed without purification by heating at reflux for 40 min with 250 mL $H_2O$ and 34 g (0.85 mol) NaOH. The ethanol formed was fractionally distilled through a 6" Vigreux column to an endpoint of 100° C. (which is the temperature of the vapors from the boiling solution). The solution was cooled to room temperature, extracted with 100 mL pentane to remove any residual mineral oil from the NaH, acidified with 24 mL concentrated $H_2SO_4$ (0.451 mol) added dropwise, then decarboxylated at reflux for 3 days (at about 100° C.) at which time no more $CO_2$ was evolved. The reaction was cooled slowly, the product isolated by filtration, washed with 50 mL $H_2O$ on the filter and dried to constant weight at 85° C. to give 42.7 g (98%) of a tan colored solid. The product, Compound 3, had the expected $^{13}C$ NMR, DEPT assignments and $^1H$ NMR spectra. $^{13}C$ NMR ($d_6$-DMSO): δ 182.6 ($C_q$), 139.6 ($C_q$), 128.9 (CH), 126.5 (CH), 38.8 ($CH_2$), 28.7 ($CH_2$). $^1H$ NMR ($d_6$-DMSO): δ 7.11 (m, 4.3H), 2.82 (m, 4.0H), 2.36 (m, 3.8H).

Step 3. Preparation of diethyl 3,3'-(1,2-phenylene)dipropionate (Compound 4)

A mixture of 41.7 g (188 mmol) Compound 3, 150 mL (2.58 mol) 100% ethanol, and 1.9 g concentrated $H_2SO_4$ (1.9 mmol) was heated at reflux overnight and then cooled to room temperature. To the room temperature reaction mixture, 2.8 g $K_2CO_3$ in 6 mL $H_2O$ added. The resulting reaction mixture was filtered and about 500 mg solid was extracted into 200 mL diethylether. The mixture was washed once with 30 ml of a saturated NaCl solution, and filtered through 4A molecular sieves to remove trace water. The diethyl ether was then removed on a rotary evaporator. The crude oil was then distilled on a Kugelrohr apparatus using a temperature of 100° C. at 200 mTorr to give 43 g (82%) oil. The product, Compound 4, had the expected $^{13}C$ NMR, DEPT assignments and $^1H$ NMR spectra. $^{13}C$ NMR($CDCl_3$): δ 172.7 ($C_q$), 138.3 ($C_q$), 128.9 (CH), 126.6 (CH), 60.4 ($CH_2$), 35.3 ($CH_2$), 27.5 ($CH_2$), 14.2 ($CH_3$). $^1H$ NMR($CDCl_3$): δ 7 (m, 7.15H), 4.13 (q, 4.0H), 2.98 (t, 4.0H), 2.60 (t, 3.8H), 1.23 (t, 5.9H).

Step 4. Preparation of 3,3'-(1,2-phenylene)bis(propan-1-ol) (Compound 5)

To a dry flask under $N_2$ were added 160 mL anhydrous diethylether and 6.6 g (174 mmol) $LiAlH_4$ pellets and stirred mechanically overnight. To this were added 43 g (155 mmol) Compound 4 in 202 mL anhydrous diethylether dropwise over 40 min. Only part of the addition was exothermic and much insoluble solid formed. 250 mL anhydrous tetrahydrofuran (THF) were added and the mixture heated at reflux overnight. The reaction mixture was cooled to 0° C. and quenched with 33 mL 1:1 THF:$H_2O$, then 9.2 g NaOH in 92 mL $H_2O$ added. The clear supernatant was decanted from the granular solid through a fluted filter paper and the solid washed with 100 mL diethylether. The combined ether solution was reduced on a rotary evaporator using a temperature of 55° C. at 288 mTorr on a Kugelrohr apparatus to give 29 g (67%) orange oil whose gas chromatography/mass spectroscopy (GCMS) showed a single component. No molecular ion was seen, but the largest peak was at 176 (M-$H_2O$). The product, Compound 5, had the expected $^{13}C$ NMR, DEPT assignments and $^1H$ NMR spectra. $^{13}C$ NMR($CDCl_3$): δ 139.9 ($C_q$), 129.3 (CH), 126.2 (CH), 62.1 ($CH_2$), 34.2 ($CH_2$), 29.0 ($CH_2$). $^1H$ NMR ($CDCl_3$): δ 7.23 (m, 4.3H), 4.39 (b, 1.9H), 3.74 (m, 4.0H), 2.81 (m, 4.0H)

Step 5. Preparation of 1,2-phenylenebis(propane-3,1-diyl) bis(4-methylbenzenesulfonate) (Compound 6)

In an Erlenmeyer flask were combined 29.0 g (149 mmol) Compound 5, 110 mL (1.4 mol) anhydrous pyridine, and 200 mL amylene stabilized $CHCl_3$. The mixture was cooled to 8° C. in an ice bath and 57.1 g (298 mmol)p-toluenesulfonyl-chloride added all at once. The mixture was stirred with a magnetic stirrer. The temperature rose to 22° C. The mixture was stirred 1 hr then poured into a separatory funnel containing 87 mL concentrated HCl and 410 mL $H_2O$. The lower layer was separated, washed once with 100 mL of a saturated NaCl solution, the volatiles removed on a rotary evaporator and then dried on a Kugelrohr apparatus using a temperature of 60° C. at 274 mTorr to give 78 g (96%) orange resin. The tosylate product, Compound 6, had the expected $^{13}C$ NMR, DEPT assignments and $^1H$ NMR spectra. $^{13}C$ NMR($CDCl_3$): δ 144.7 ($C_q$), 138.0 ($C_q$), 132.7 (CH), 129.7 (CH), 124.3 (CH), 127.7 (CH), 126.4 (CH), 69.7 ($CH_2$), 29.9 ($CH_2$), 28.0 ($CH_2$), 21.5 ($CH_3$). $^1H$ NMR ($CDCl_3$): δ 7.80 (d, 4.0H), 7.36 (d, 3.9H), 7.09 (m, 2.5H), 7.00 (m, 2.1H), 4.06 (t, 3.7H), 2.59 (m, 3.7H), 2.45 (s, 5.9H), 1.89 (m, 4.1H).

Step 6. Preparation of 1,2-bis(3-(pyrrolidin-1-yl)propyl)benzene (Compound 7)

To 71.8 g (143 mmol) Compound 6 in 216 g amylene stabilized $CHCl_3$ were added 83 mL (1.01 mol) pyrrolidine and the mixture heated at reflux 1 hr, cooled to room temperature and poured into 400 mL $H_2O$ containing 39 g NaOH. The layers were separated, the $CHCl_3$ layer washed once with 300 mL $H_2O$, the volatiles removed on a rotary evaporator and the product distilled on a Kugelrohr apparatus to give 36.5 g (85%) colorless oil having a boiling point in the range of 195-215° C. at 300 mTorr. GCMS showed the expected product (M-1=299) with ~5% of 1-tosylpyrrolidine impurity. The pyrrolidine product, Compound 7, had the expected $^{13}C$ NMR, DEPT assignments and $^1H$ NMR spectra. $^{13}C$ NMR($CDCl_3$): δ 140.0 ($C_q$), 129.1 (CH), 125.8 (CH), 56.3 ($CH_2$), 54.2 ($CH_2$), 30.6 ($CH_2$), 30.6 ($CH_2$), 23.5 ($CH_2$). $^1H$ NMR($CDCl_3$): δ 7.12 (m, 4.1H), 2.66 (m, 4.1H), 2.49 (m, 11.6H), 1.67 (m, 12.2H).

Step 7. Preparation of 1,1'-(1,2-phenylenebis(propane-3,1-diyl))bis(1-ethylpyrrolidin-1-ium) Iodide (Compound E, Anion is Iodide)

To a 3-necked jacketed flask equipped with a condenser and an addition funnel were added (46.4 g, 154 mmol) of the Compound 7 dissolved in 200 mL of $CH_3CN$. 90 mL (175 g, 1.12 mol) iodoethane was added in 10 mL increments to the reaction. No reaction or exotherm was noted. The mixture was heated with steam in the jacket. At or near reflux, much solid precipitated. An additional 200 mL $CH_3CN$ was added and the mixture heated at reflux overnight. The mixture was cooled to room temperature, filtered, subjected to a vacuum such that most of the solvent was removed while placed under a rubber dam, and the solid dried to a constant weight in an oven at 60° C. to yield 79.4 g (84%) a pale tan colored solid. The product had the expected $^{13}C$ NMR, DEPT assignments and $^1H$ NMR spectra. $^{13}C$ NMR ($d_6$-DMSO): δ 138.9 ($C_q$), 129.6 (CH), 126.9 (CH), 62.3 ($CH_2$), 58.3 ($CH_2$), 54.7 ($CH_2$), 28.7 ($CH_2$), 24.9 ($CH_2$), 22.0 ($CH_2$), 9.2 ($CH_3$). $^1H$ NMR ($d_6$-DMSO): δ 7.30 (m, 1.97H), 7.18 (m, 2.02H), 3.58-3.37 (m+s at 3.47, 44.08H), 2.45 (m, 4.16H), 2.06 (m, 7.71H), 1.87 (m, 3.72H) 1.21 (t, 5.62H).

Step 8. Preparation of 1,1'-(1,2-phenylenebis(propane-3,1-diyl))bis(1-ethylpyrrolidin-1-ium) Hydroxide (Compound E, Anion is Hydroxide)

The 79.4 g Compound E, anion is iodide, obtained in the previous step was added to 400 mL Dowex® SBR LC NG (OH) resin or Dowex® Monosphere™ 550A UPW OH resin which had been washed twice with $H_2O$ in a 1 L plastic bottle. To this was added enough water to fill the bottle leaving about 1" of head-space. The bottle was sealed and rolled at 10 revolutions per minute (RPM) for 1 hour, filtered, the resin washed with about 800 mL $H_2O$ so the final pH of the last drop from the wash was ~11. The solution was reduced to 316 g by rotary evaporation using a temperature of 50° C. at 30 mBar. 2.216 g of that solution was diluted to 25 mL of which 5.75 mL was required to titrate 83.1 mg potassium hydrogen phthalate to a phenolphthalein endpoint. Based on the titration values, it was calculated that the 25 mL diluted solution contained 15.7 wt. % Compound E with the anion being hydroxide. Integration of the organic hydrogens against the water hydrogens in this solution using $^1H$ NMR gave 15.5 wt. %. The average of these determinations (i.e., average of NMR and titration determinations) 15.6 wt. %, calculates to a conversion of 97%. The $^{13}C$ NMR was unchanged from the spectrum seen for the iodide form. The $^{14}N$ NMR ($H_2O/D_2O$) gave a single, sharp peak (11 Hz half width) at 59.0 ppm consistent with the expected structure.

Alternative procedures to prepare to Compound E is described below. Step 1A.

Preparation of tetraethyl 2,2'-(1,2-phenylenebis(methylene)) dimalonate (Compound 2)

In a 3-L, 3-necked flask equipped with a mechanical stirrer and cooling jacket under flowing nitrogen was charged with 66.5 g 60 wt. % NaH (1.66 mol). 650 mL dry DMF was added and the mixture was stirred at 0° C. 365 mL diethylmalonate (2.40 mol) was dropped in via addition funnel; during the addition, the temperature rose to between 5 and 18° C. The reaction was then stirred for 1 hour until all the NaH was dissolved. Compound 1 (105.1 g, 0.60 mol) was dissolved in 200 ml of dry DMF and added drop wise while maintaining a reaction temperature of 0 to 70° C. during the addition. After the addition, the beige mixture was stirred at 0° C. for two days.

After two days of mixing, with the mixture at 0° C., most of a 1000 mL quantity of water solution containing 37 mL of concentrated HCl was added and the mixture was then allowed to warm to room temperature. The brown mixture was then transferred to a 4-L separatory funnel. The lower layer was removed and then placed in a 2-L round-bottom flask. The solvent was then removed by rotoevaporation to obtain 408.1 g of a dark orange solution. The solution was placed on a Kugelrohr and the dimalonate product was isolated at 180° C. and 438 mTorr—the dimalonate product was a dark red oil (135 g, 53%).

Step 2A. Preparation of 3,3'-(1,2-phenylene)dipropionic acid (Compound 3)

The dimalonate product (Compound 2) was transferred to a 2-L single-necked round bottom flask and 155 mL ethanol was added (dark brown solution). A solution of NaOH 65 g in 450 mL water was added and the reaction was heated to reflux with vigorous stirring. After 35 minutes, the dark brown solution was allowed to cool down. A six-inch Vigreux column was connected to the reaction vessel. The temperature was raised to 98-102° C., whereby 300 mL of ethanol and water was distilled. The distillation head was removed and replaced with a dropping funnel containing 50 mL of concentrated sulfuric acid. The acid was added drop-wise over 30 minutes. The dropping funnel was removed and replaced with a condenser and the reaction refluxed for 24 hours at which time a brown precipitate formed. The precipitate was filtered and dried overnight at 80° C. to yield (84 g, 100%) of desired di-acid product (Compound 3) as a brown crusty material.

Step 3A. Preparation of diethyl 3,3'-(1,2-phenylene)dipropionate (Compound 4)

In a 1-L round bottom flask was added 84 g (0.37 mol) of the di-acid (Compound 3), 610 mL of absolute ethanol, and 5 g of concentrated sulfuric acid. The mixture was stirred and heated at reflux overnight. The reaction was cooled to room temperature and 10 g (0.07 mol) and potassium carbonate was added at once with stirring. Concentrating in vacuo at 62° C., 207 mbar yielded 590 mL of distillate. 500 mL of ether and 60 mL of 5% sodium bicarbonate were added and the mixture was stirred at room temperature. The biphasic brown solution was then poured into a separatory funnel. The layers were separated. The ether layer was dried over 4 Å molecular sieves and concentrated in vacuo 51° C., 847 mbar then 60° C., 136 mbar. 92 g of a brown runny oil was recovered. The oil was placed on Kugelrohr at 90° C., 261 mTorr to recover (89 g, 86%) of the diester (Compound 4).

Step 4A. Preparation of 3,3'-(1,2-phenylene)bis(propan-1-ol) (Compound 5)

An oven-dried 3-L round bottom jacketed flask equipped with a dropping funnel, reflux condenser, and mechanical stirrer was assembled hot and cooled under flowing nitrogen. It was then charged with 540 mL of dry tetrahydrofuran and 19.8 g of lithium aluminum hydride pellets. The gray mixture was stirred for 30 minutes. 89 g of diester (Compound 4) dissolved in 170 mL of dry tetrahydrofuran was added dropwise over 1 hour. The reaction was exothermic and after the addition, the mixture was refluxed gently for 1 hour. The reaction was then cooled to 0° C. and quenched with 1:1 THF:water and 26 g of sodium hydroxide in 270 mL of water. The resulting slurry was filtered through a Buchner funnel and the solid was washed with 500 mL of ether. The solvent was removed via rotovap 70° C., 151 mbar to recover 63.7 g of a brown oil. The brown oil was placed on a Kugelrohr at 100° C., 1.64 torr to recover (61.1 g, 98.5%) of the diol (Compound 5).

Step 5A. Preparation of 1,2-phenylenebis(propane-3,1-diyl) bis(4-methylbenzenesulfonate) (Compound 6)

Diol (Compound 5) 61.1 g was dissolved in 230 mL of pyridine and poured into a 1 L Erlenmeyer. The round bottom flask was rinsed with a total of 425 mL of chloroform. The Erlenmeyer was cooled to 0° C. in a water/carbon dioxide cooling bath and 120 g of tosyl chloride was added quickly with stirring and the temperature rose to 10° C. After 20 minutes, the temperature remained at 10° C. The flask was removed from its cooling bath, allowed to warm to room temperature, and stirred for 35 minutes. The yellow orange solution was poured into a 2-L separatory funnel containing 183 mL of concentrated hydrochloric acid and 840 mL of water. The layers were separated and the lower layer was washed with 210 mL of saturated aqueous sodium chloride. The lower layer was poured through 4 Å sieves and concentrated in vacuo 60° C., 151 mTorr to give 160.8 g of a dark orange oil which was further distilled in a Kugelrohr at 60° C., 261 mTorr to recover (143.6 g, 91%) of the ditosylate (Compound 6) as a dark orange oil.

Step 6. Preparation of 1,2-bis(3-(pyrrolidin-1-yl)propyl)benzene (Compound 7)

91.5 g of ditosylate (Compound 6) was dissolved in 100 mL of acetonitrile. 106 mL of pyrrolidine was added dropwise to this solution over 20-40 minutes. The solution warmed slightly. The flask was stoppered and left to stand overnight. The brown solution was poured into a 2-L round bottom flask and concentrated in vacuo at 50° C., 150 mbar. A solution of 40 g of NaOH in 400 mL of water was added and the biphasic layer was stirred with a stir bar for 10 minutes, then placed in a 1-L separatory funnel and shaken. The layers were separated and the ether layer was washed with 50 mL of saturated aqueous sodium chloride. The organic layer was concentrated at 60° C., 150 mbar to recover 53.6 g of a dark brown solution. The material was further distilled in a Kugelrohr at 195° C., 245 mTorr to recover (46.48 g, 85%) of the dipyrrolidino product (Compound 7) as a pale yellow oil.

Step 7A. Preparation of 1,1'-(1,2-phenylenebis(propane-3,1-diyl))bis(1-ethylpyrrolidin-1-ium) Iodide (Compound E, Anion is Iodide)

To a 3-necked jacketed flask equipped with a condenser and addition funnel was added (46.4 g, 154 mmol) of the dipyrrolidino product (Compound 7) dissolved in 200 mL of acetonitrile. 90 mL (175 g, 1.12 mol) iodoethane was added in 10 mL increments to the reaction. After all the reagent was added, the reaction was heated to reflux using steam. Upon heating a white precipitate formed. An additional 200 mL of acetonitrile was added to aid stirring and the reaction refluxed overnight. The heating was stopped and the reaction was cooled to room temperature. The reaction flask was wrapped in aluminum foil while cooling. The reaction mixture was filtered through a Buchner funnel and the mostly white solid was rinsed with ether (120 mL). The white solid was dried with a rubber dam under full house vacuum. The white material was then placed in a crystallization dish and dried in a 60° C. oven. (79.4 g, 84%) of desired diquaternary ammonium salt product (Compound E, anion is iodide) was obtained.

Step 8A. Preparation of 1,1'-(1,2-phenylenebis(propane-3,1-diyl))bis(1-ethylpyrrolidin-1-ium) Hydroxide (Compound E, Anion is Hydroxide)

The diiodide product (Compound E, anion is iodide) (79.4 g, 0.13 mol) was dissolved in water and ion exchanged by passing through a column of Dowex® Monosphere™ 550A OH resin. The dihydroxy compound (Compound E, anion is hydroxide) was collected and concentrated to a 15 wt. % solution.

Example 2: Additional Synthesis of Compound E

Alternatively, Compound E can be prepared according to Scheme 2.

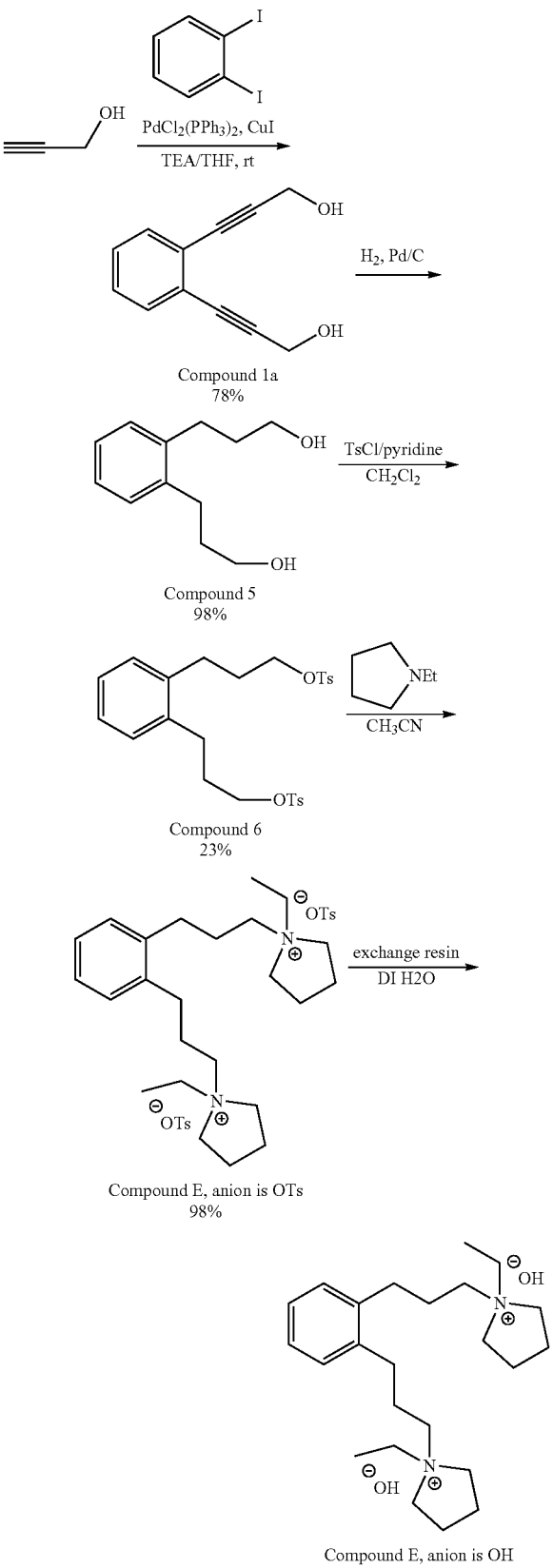

Step 1. Preparation of 3,3'-(1,2-phenylene)bis(prop-2-yn-1-ol) (Compound 1a)

Synthesis of 3,3'-(1,2-phenylene)bis(prop-2-yn-1-ol) was prepared according to the procedures reported in *J. Phys. Org. Chem.*, 2011, 24, 969-975. In a dry 3-neck 2 L round bottom flask with a mechanical stirrer attached was added 1,2 diiodobenzene (36.0 g; 109.1 mmol) in dry THF (720 mL) under nitrogen. The solution was evacuated and refilled with nitrogen twice. Bis(triphenylphosphine)palladium dichloride (7.2 g; 10.3 mmol, 0.09 mol. %) was added in one portion. Again the system was evacuated and refilled with nitrogen twice. Copper (I) iodide (1.2 g; 6.5 mmol, 0.06 mol. %) was added and the dark orange mixture was stirred for 5 minutes. Propargyl alcohol (25.4 mL; 436.3 mmol, 4.0 eq.) was added quickly via a syringe followed by diethylamine (72 mL). The dark brown solution was wrapped in aluminum foil and stirred overnight. Thin Layer Chromatography (TLC) (95:5 hexane:ethyl acetate with UV detection) indicated a minor amount of starting material remained. Propargyl alcohol (12.7 mL; 218.1 mmol, 2.0 eq.) was added followed by diethylamine (36 mL). After another 48 hours (72 hours total) the reaction solution was concentrated in vacuo to recover a viscous oil as crude product. The crude product was dissolved (with warming) in 800 mL of ethyl acetate and 1M HCl (250 mL). The mixture was filtered and poured into a 2 L separatory funnel. The contents were shaken and separated. The organic layer was washed with water (2×200 mL) and brine (250 mL). The organic layer was concentrated in vacuo to recover 22.0 g of a brown oil, which was pre-adsorbed onto silica and isolated using silica gel chromatography. The product was isolated using a continuous gradient of 40 to 70 vol. % ethyl acetate:hexane over 35 minutes to recover 12.7 g (62%) of desired product. $^1$H-NMR, 400 MHz, CDCl$_3$, ppm; 7.4-7.3 (m, 2H), 7.2 (m, 2H), 4.5 (s, 4H) and 3.5 (br, 2H). $^{13}$C-NMR, 100 MHz, CDCl$_3$, ppm; 131.5, 128.0, 125.2, 91.6, 84.2 and 51.4.

Step 2. Preparation of 3,3'-(1,2-phenylene)bis(propan-1-ol) (Compound 5)

3,3'-(1,2-phenylene)bis(prop-2-yn-1-ol) (12.6 g; 67.6 mmol) was dissolved in 100 mL of THF and 67 mL of methanol with warming. The light brown solution was poured into a 600 mL stainless steel autoclave. Palladium (2.5 g, 10% on charcoal) was added as a slurry in 171 mL of THF to create a final concentration of compound 1a of 0.2 M. The slurry was heated to 100° C. under 900 psi H2 for 30 hours with a stirring rate of 750 RPM. After 30 hours, an aliquot was sampled for analysis. $^1$H-NMR(CDCl$_3$) indicated the reaction was complete. The reaction mixture was filtered through a pad of Celite and rinsed with 200 mL of THF. The solvent was concentrated in vacuo to recover 13.3 g of a dark oil. The crude product was pre-adsorbed onto silica and was isolated using silica gel chromatography. The product was isolated using a continuous gradient of 0 to 100 vol. % ethyl acetate:hexane over 30 minutes to recover 9.9 g (75%) of the desired product as a pale yellow oil which solidified overnight. $^1$H-NMR, 400 MHz, CDCl$_3$, ppm; 7.1-7.0 (m, 4H), 3.6 (t, 4H), 3.0 br, 2H), 2.7 (m, 4H), 1.8-1.7 (m, 4H). $^{13}$C-NMR, 100 MHz, CDCl$_3$, ppm; 139.8, 129.2, 126.1, 62.2, 34.1 and 28.8.

Step 3. Preparation of 1,2-phenylenebis(propane-3,1-diyl)bis(4-methylbenzenesulfonate) (Compound 6)

In a 500 mL round bottom flask 3,3'-(1,2-phenylene)bis(propan-1-ol) (12.2 g; 62.7 mmol) was dissolved into CHCl$_3$ (126 mL, amylene stabilized) under nitrogen. Triethylamine (17.8 mL; 127.4 mmol) was added and the solution was cooled to −5° C. (4:1 IPA:water with CO$_2$ (s)). 4-(Dimethylamino) pyridine (0.3 g; 3.1 mmol) was added. After 5 minutes, p-toluenesulfonylchloride (24.3 g; 127.4 mmol, recrystallized from hexane) was added. After 10 minutes the reaction was allowed to warm to room temperature. The reaction was stirred at room temperature for 5 hours. $^1$H-NMR of an aliquot indicated the reaction was complete. The reaction solution was poured into a separatory funnel and washed with 150 mL of aqueous acid solution (51 mL of concentrated HCl in 240 mL of deionized water), saturated ammonium chloride (150 mL) and brine (150 mL). The organic layer was concentrated in vacuo to recover 30.5 g (96%) of crude desired product. $^1$H-NMR, 400 MHz, CDCl$_3$, ppm; 7.8-7.7 (d, 4H), 7.3 (d, 4H), 7.1 (m, 2H), 7.0 (m, 2H), 4.0 (t, 4H), 2.6-2.5 (m, 4H), 2.4 (s, 6H), 1.8 (m, 4H). $^{13}$C-NMR, 100 MHz, CDCl$_3$, ppm; 144.8, 138.2, 133.0, 129.9, 129.1, 127.9, 126.5, 69.7, 30.0, 28.1 and 21.6.

Step 4. Preparation of 1,1'-(1,2-phenylenebis(propane-3,1-diyl))bis(1-ethylpyrrolidin-1-ium) 4-methylbenzenesulfonate (Compound E, anion is tosylate)

In a dry 2 neck 100 mL round bottom flask with stir bar was added 1,2-phenylenebis(propane-3,1-diyl)bis(4methylbenzenesulfonate) (5.0 g; 9.9 mmol) dissolved in 20 mL of dry acetonitrile under nitrogen. N-ethylpyrrolidine (2.5 mL, 20.8 mmol, 2.1 eq.) was added and the solution was heated to reflux for 3.5 hours. $^1$H-NMR of an aliquot indicated the reaction was complete. The reaction solution was concentrated in vacuo at 55° C. until a constant weight. 6.9 g (99%) of crude product was recovered. $^1$H-NMR, 400 MHz, CD$_3$CN, ppm; 7.6 (d, 4H), 7.2-7.1 (m, 8H), 3.4-3.3 (m, 12H), 3.2 (q, 4H), 2.7 (m, 4H), 2.3 (s, 6H), 2.0-1.9 (m, 12H) and 1.2-1.1 (m, 6H). $^{13}$C-NMR, 100 MHz, CD$_3$CN, ppm; 145.4, 138.4, 138.3, 129.0, 128.0, 126.3, 125.3, 61.7, 58.2, 54.1, 28.1, 24.6, 21.1, 19.9 and 7.7.

Step 5. Preparation of 1,1'-(1,2-phenylenebis(propane-3,1-diyl))bis(1-ethylpyrrolidin-1-ium) hydroxide (Compound E, anion is hydroxide)

The tosylate salt 1,1'-(1,2-phenylenebis(propane-3,1-diyl))bis(1-ethylpyrrolidin-1-ium) 4-methylbenzenesulfonate was converted to the hydroxide salt using similar procedures as in Step 8 of the Example 1.

Example 3: Synthesis of as-made EMM-31 Using Sodium-Containing Regent

To 14.1 ml of a 15.60 wt. % solution of the SDA (Compound E in its hydroxide form) were added 1.38 ml of a 10 wt. % NaOH solution and 13.4 ml of a 3.47 wt. % solution of boric acid. To this was then added 6.25 mL of LUDOX® LS-30 and 0.40 ml of deionized water. The 45-mL Teflon liner was then capped and sealed within a steel Parr autoclave and heated at 160° C. over the course of 21 days in a convection oven. The product was recovered by filtration and washed with deionized water. The resulting product was analyzed by power XRD as shown in FIG. 1 and Table 4 provides the peak listing.

TABLE 4

| degree 2-theta | d-spacing (Å) | relative intensity [100 × I/(Io)] |
|---|---|---|
| 6.32 | 13.98 | 66 |
| 7.68 | 11.50 | 31 |
| 8.17 | 10.82 | 84 |
| 8.67 | 10.19 | 19 |
| 9.26 | 9.54 | 17 |
| 9.68 | 9.13 | 2 |
| 10.74 | 8.23 | 4 |
| 12.73 | 6.95 | 12 |
| 13.34 | 6.63 | 12 |
| 14.56 | 6.08 | 2 |
| 15.43 | 5.74 | 21 |
| 15.89 | 5.57 | 4 |
| 16.52 | 5.36 | 4 |
| 17.13 | 5.17 | 5 |
| 18.35 | 4.830 | 23 |
| 19.31 | 4.594 | 90 |
| 20.19 | 4.396 | 48 |
| 21.35 | 4.158 | 97 |
| 21.75 | 4.083 | 59 |
| 22.84 | 3.890 | 100 |
| 23.46 | 3.790 | 51 |
| 25.14 | 3.539 | 29 |
| 25.84 | 3.445 | 43 |
| 26.40 | 3.373 | 28 |
| 26.89 | 3.314 | 42 |
| 27.64 | 3.225 | 5 |
| 28.35 | 3.145 | 2 |
| 29.06 | 3.070 | 35 |
| 29.80 | 2.996 | 10 |
| 30.80 | 2.900 | 13 |
| 32.51 | 2.752 | 3 |
| 33.57 | 2.668 | 37 |
| 34.20 | 2.620 | 47 |
| 35.08 | 2.556 | 10 |
| 35.39 | 2.534 | 3 |
| 36.12 | 2.485 | 3 |
| 36.88 | 2.436 | 3 |
| 38.87 | 2.315 | 2 |

The synthesis was repeated except that seeds of EMM-31 were used. After 29 days of heating at 160° C. the product was isolated as described previously. The powder XRD pattern showed the sample to be EMM-31 (data not shown). This synthesis using seeds of EMM-31 was repeated except the reaction was heated at 180° C. over the course of 6 days or at 175° C. over the course of 7 days. Powder XRD showed the products to be EMM-31 (data not shown). This synthesis using seeds of EMM-31 was repeated except the reaction was heated at 150° C. with the following molar ratios of NaOH/Si=0.10, SDA(OH)$_2$/Si=0.25, Si/B=10, and H$_2$O/Si=30. After 21 days of heating, the products were amorphous.

Example 4: Synthesis of as-made EMM-31 Using Potassium-Containing Regent

To 184 µL of a 15.60 wt. % solution of the SDA (Compound E in its hydroxide form) were added 20.53 µL of a 17.5 wt. % KOH solution and 131.5 µL of a 3.47 wt. % solution of boric acid. To this was then added 122.2 µL of LUDOX® LS-30 and 7.6 µL of deionized water. The 1.5 ml SS liner was then capped and sealed in a high-throughput, 24-well aluminum autoclave block and heated at 160° C. over the course of 21 days. The product was recovered by centrifugation and washed with deionized water. The resulting product was analyzed by power XRD as shown in FIG. 2 and Table 5 provides the peak listing.

TABLE 5

| degree 2-theta | d-spacing (Å) | relative intensity [100 × I/(Io)] |
|---|---|---|
| 6.34 | 13.92 | 47 |
| 7.75 | 11.39 | 17 |
| 8.25 | 10.71 | 48 |
| 8.71 | 10.14 | 28 |
| 9.32 | 9.48 | 13 |
| 9.80 | 9.02 | 4 |
| 10.85 | 8.15 | 4 |
| 12.84 | 6.89 | 4 |
| 13.28 | 6.66 | 3 |
| 15.47 | 5.73 | 15 |
| 16.61 | 5.33 | 6 |
| 17.18 | 5.16 | 7 |
| 18.46 | 4.8 | 17 |
| 18.74 | 4.73 | 4 |
| 19.37 | 4.58 | 61 |
| 20.27 | 4.38 | 30 |
| 21.40 | 4.15 | 56 |
| 21.90 | 4.05 | 11 |
| 22.17 | 4.01 | 4 |
| 22.49 | 3.95 | 3 |
| 22.92 | 3.88 | 100 |
| 23.51 | 3.78 | 36 |
| 25.20 | 3.53 | 11 |
| 25.62 | 3.47 | 9 |
| 25.96 | 3.43 | 16 |
| 26.36 | 3.38 | 10 |
| 26.98 | 3.3 | 23 |
| 27.72 | 3.22 | 7 |
| 29.11 | 3.07 | 21 |
| 29.91 | 2.99 | 7 |
| 30.90 | 2.89 | 10 |
| 33.76 | 2.65 | 8 |
| 34.29 | 2.61 | 11 |
| 34.53 | 2.6 | 5 |

The synthesis was repeated except that seeds of EMM-31 were used. After 29 days of heating at 160° C. the product was isolated as described previously. The powder XRD pattern showed the sample to be EMM-31 (data not shown). This synthesis using seeds of EMM-31 was repeated except the reaction was heated at 180° C. over the course of 6 days or 175° C. over the course of 7 days. Powder XRD showed the product to be EMM-31 (data not shown). This synthesis using seeds of EMM-31 was repeated except the reaction was heated at 150° C. with the following molar ratios of KOH/Si=0.10, SDA(OH)$_2$/Si=0.25, Si/B=10, and H$_2$O/Si=30. After 21 days of heating, the products were amorphous.

Example 5: Thermally-Treated EMM-31

A sample of the as-made EMM-31 material prepared using a sodium-containing reagent (Example 3 synthesized without seeds) was calcined to 540° C. The sample was calcined in a muffle furnace by introducing N$_2$ to the furnace at room temperature for 2 hours, then ramping the temperature of the N$_2$ atmosphere within the furnace to 400° C. at 2° C./min, and then introducing air while ramping the temperature of the atmosphere within the furnace to 540° C. at 2° C./min. The temperature was held at 540° C. for 2 hours before the sample was allowed to cool to room temperature.

The thermally-treated sample was measured with nitrogen physisorption and the data analyzed using the t-plot method. The material possessed 0.22 cc/g micropore volume and 75 m$^2$/g external surface area. This thermally-treated EMM-31 was converted to an aluminosilicate by adding 1.03 g of the thermally-treated EMM-31 to 20 mL of 1M Al$_2$(SO$_4$)$_3$ solution and heating the suspension in a sealed autoclave in a convection oven overnight maintained at 100° C. The product was recovered by filtration and washed with about 250 mL deionized water. A sample of the alumniosilicate EMM-31 material was measured with the alpha (n-hexane cracking) test. The measured alpha value was 140.

Figure 3:
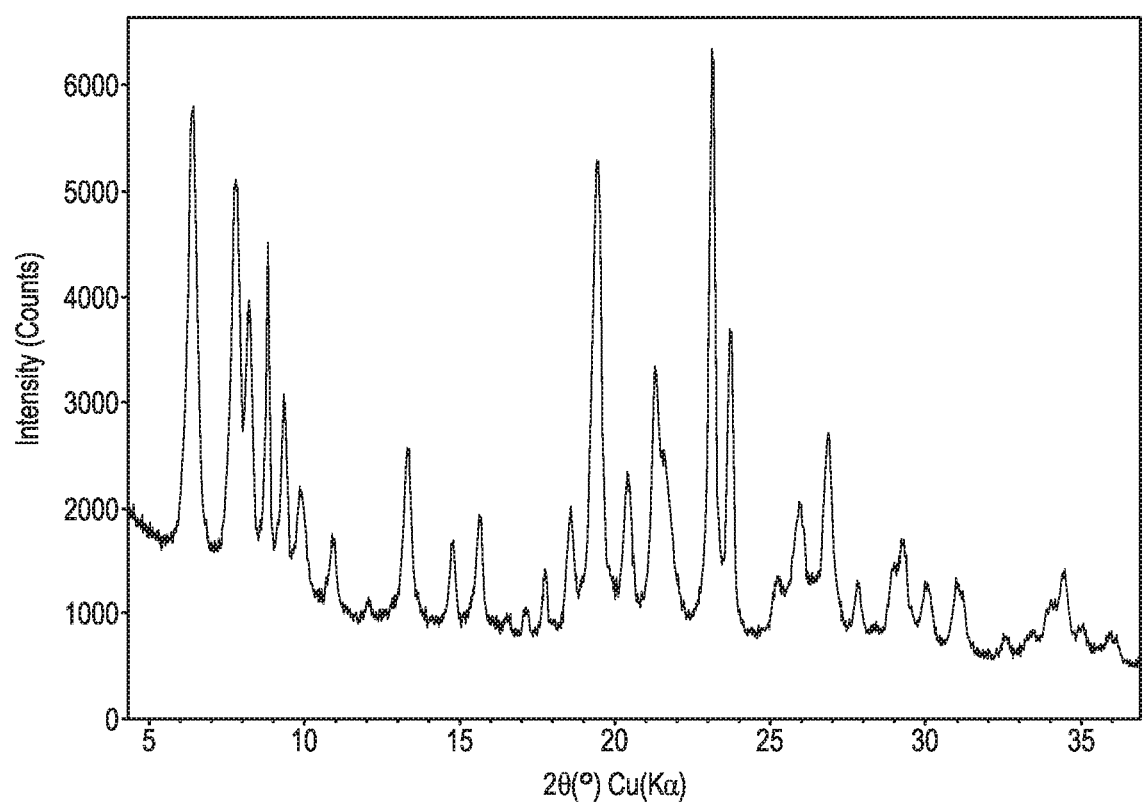
FIG. 3 shows a powder XRD pattern of a thermally-treated EMM-31 material.

A sample of an as-made EMM-31 synthesized using a sodium-containing reagent from Example 3 was calcined to 540° C. The resulting product (thermally treated EMM-31 material) was analyzed by power XRD as shown in FIG. 3 and Table 6 provides the peak listing.

TABLE 6

| degree 2-theta | d-spacing (Å) | relative intensity [100 × I/(Io)] |
| --- | --- | --- |
| 6.39 | 13.81 | 80 |
| 7.78 | 11.35 | 71 |
| 8.22 | 10.75 | 31 |
| 8.82 | 10.02 | 29 |
| 9.34 | 9.47 | 19 |
| 9.89 | 8.94 | 14 |
| 10.91 | 8.10 | 9 |
| 12.06 | 7.33 | 2 |
| 13.31 | 6.65 | 32 |
| 14.75 | 6.00 | 8 |
| 15.61 | 5.67 | 16 |
| 16.51 | 5.36 | 1 |
| 17.11 | 5.18 | 1 |
| 17.73 | 5.00 | 5 |
| 18.54 | 4.78 | 13 |
| 19.40 | 4.57 | 100 |
| 20.41 | 4.35 | 26 |
| 21.30 | 4.17 | 41 |
| 21.59 | 4.11 | 11 |
| 21.76 | 4.08 | 18 |
| 23.13 | 3.84 | 78 |
| 23.71 | 3.75 | 27 |
| 25.27 | 3.52 | 10 |
| 25.91 | 3.44 | 27 |
| 26.41 | 3.37 | 4 |
| 26.84 | 3.32 | 46 |
| 27.81 | 3.21 | 7 |
| 28.34 | 3.15 | 2 |
| 28.92 | 3.08 | 7 |
| 29.26 | 3.05 | 25 |
| 30.03 | 2.97 | 11 |
| 31.00 | 2.88 | 11 |
| 31.21 | 2.86 | 3 |
| 32.54 | 2.75 | 2 |
| 33.38 | 2.68 | 7 |
| 34.00 | 2.64 | 9 |
| 34.43 | 2.60 | 17 |
| 35.01 | 2.56 | 9 |
| 35.92 | 2.50 | 7 |
| 37.06 | 2.42 | 2 |
| 37.46 | 2.40 | 3 |

Various modifications of the disclosure, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A crystalline material having the XRD peaks of Table 1:

TABLE 1

| degree 2-theta (±0.2) | relative intensity [100 × I/(Io)] |
| --- | --- |
| 6.39 | 60-100 |
| 7.78 | 60-80 |

TABLE 1-continued

| degree 2-theta (±0.2) | relative intensity [100 × I/(Io)] |
| --- | --- |
| 8.22 | 20-40 |
| 8.82 | 20-40 |
| 9.34 | 10-30 |
| 9.89 | 5-25 |
| 13.31 | 20-40 |
| 19.40 | 60-100 |
| 23.13 | 60-90 |
| 23.71 | 15-35 | wherein the material contains a structure directing agent and part or all of the structure directing agent is removed.

2. The material of claim 1 having a micropore volume of 0.10 to 0.25 cc/g.

3. The material of claim 1 having a C-centered unit cell a-parameter of 17.9±0.5 Å, b-parameter of 21.4±0.5 Å, and c-parameter of 20.0±0.5 Å.

4. The material of claim 1, wherein the material is suitable for adsorbing 60 to 150 mg/g of n-hexane or 40 to 100 mg/g of mesitylene.

5. The material of claim 1 having the XRD peaks:

| degree 2-theta (±0.2) | relative intensity [100 × I/(Io)] |
| --- | --- |
| 6.39 | 60-100 |
| 7.78 | 60-80 |
| 8.22 | 20-40 |
| 8.82 | 20-40 |
| 19.40 | 60-100 |
| 23.13 | 60-90 | and (i) has a micropore volume of 0.10 to 0.25 cc/g; (ii) has a C-centered unit cell a-parameter of 17.9±0.5 Å, b-parameter of 21.4±0.5 Å, and c-parameter of 20.0±0.5 Å; or (iii) is suitable for adsorbing 60 to 150 mg/g of n-hexane or 40 to 100 mg/g of mesitylene.

6. The material of claim 1 having Formula I:

$$(v)X_2O_3:YO_2 \quad \text{(Formula I)},$$

wherein $0.0005 \leq v \leq 0.1$, X is a trivalent element, and Y is a tetravalent element.

7. The material of claim 6, wherein the molar ratio of Y to X is 5 to 25 when X is B.

8. The material of claim 6, wherein the molar ratio of Y to X is 100 to 500 when X is Al.

9. A process of converting an organic compound to a conversion product comprising contacting the organic compound with the material of claim 1.

10. An as-made crystalline material having the XRD peaks Table 3:

TABLE 3

| degrees 2-theta (±0.2) | relative intensity [100 × I/(Io)] |
| --- | --- |
| 6.34 | 20-60 |
| 7.75 | 10-30 |
| 8.25 | 20-60 |
| 8.71 | 20-40 |
| 9.32 | 1-20 |
| 15.47 | 1-20 |
| 19.37 | 40-80 |
| 21.40 | 40-70 |
| 22.92 | 60-100 |
| 23.51 | 20-50 |

11. The material of claim 10 having a C-centered unit cell a-parameter of 17.9±0.5 Å, b-parameter of 21.3±0.5 Å, and c-parameter of 20.2±0.5 Å.

12. The material of claim 10 having Formula II:

$$(n)G:(v)X_2O_3:YO_2 \qquad \text{(Formula II)},$$

wherein 0.01≤n≤0.3, 0.0005≤v≤0.1, G is an organic structure directing agent, X is a trivalent element, and Y is a tetravalent element.

13. The material of claim 12, wherein the molar ratio of Y to X is 10 to 40 when X is B.

14. The material of claim 12 wherein the molar ratio of G to Y is 0.1 to 0.2.

15. A process of preparing the material of claim 10 comprising mixing a composition comprising a source of hydroxide ions, a source of an oxide of a tetravalent element Y, a source of a trivalent element X, and a structure directing agent comprising the following structure:

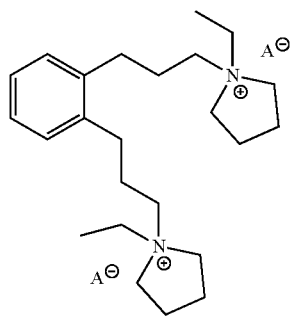

wherein A is an ion.

16. The process of claim 15 further comprises removing part or all of the structure directing agent.

17. The process of claim 15, wherein both A ions are hydroxide ions.

18. The process of claim 15, wherein the material having X is B and Y is Si is contacted with an Al source under conditions sufficient to exchange the B in the framework with Al.

19. A crystalline material having a framework defined by the following connectivities in Table 2 for the tetrahedral (T) atoms in the unit cell, the tetrahedral (T) atoms being connected by bridging atoms:

TABLE 2

| T atom | Connected to: |
| --- | --- |
| T1 | T2, T4, T37, T100 |
| T2 | T1, T3, T6, T57 |
| T3 | T2, T5, T56, T99 |
| T4 | T1, T64, T95, T121 |
| T5 | T3, T6, T65, T94 |
| T6 | T2, T5, T66, T126 |
| T7 | T8, T10, T43, T104 |
| T8 | T7, T9, T12, T51 |
| T9 | T8, T11, T50, T103 |
| T10 | T7, T70, T89, T125 |
| T11 | T9, T12, T71, T88 |
| T12 | T8, T11, T72, T122 |
| T13 | T14, T16, T25, T108 |
| T14 | T13, T15, T18, T69 |
| T15 | T14, T17, T68, T107 |
| T16 | T13, T52, T83, T113 |
| T17 | T15, T18, T53, T82 |
| T18 | T14, T17, T54, T118 |
| T19 | T20, T22, T31, T112 |

TABLE 2-continued

| T atom | Connected to: |
| --- | --- |
| T20 | T19, T21, T24, T63 |
| T21 | T20, T23, T62, T111 |
| T22 | T19, T58, T77, T117 |
| T23 | T21, T24, T59, T76 |
| T24 | T20, T23, T60, T114 |
| T25 | T13, T26, T28, T116 |
| T26 | T25, T27, T30, T81 |
| T27 | T26, T29, T80, T115 |
| T28 | T25, T71, T88, T105 |
| T29 | T27, T30, T70, T89 |
| T30 | T26, T29, T90, T110 |
| T31 | T19, T32, T34, T120 |
| T32 | T31, T33, T36, T75 |
| T33 | T32, T35, T74, T119 |
| T34 | T31, T65, T94, T109 |
| T35 | T33, T36, T64, T95 |
| T36 | T32, T35, T96, T106 |
| T37 | T1, T38, T40, T124 |
| T38 | T37, T39, T42, T93 |
| T39 | T38, T41, T92, T123 |
| T40 | T37, T59, T76, T97 |
| T41 | T39, T42, T58, T77 |
| T42 | T38, T41, T78, T102 |
| T43 | T7, T44, T46, T128 |
| T44 | T43, T45, T48, T87 |
| T45 | T44, T47, T86, T127 |
| T46 | T43, T53, T82, T101 |
| T47 | T45, T48, T52, T83 |
| T48 | T44, T47, T84, T98 |
| T49 | T50, T52, T85, T124 |
| T50 | T9, T49, T51, T54 |
| T51 | T8, T50, T53, T123 |
| T52 | T16, T47, T49, T97 |
| T53 | T17, T46, T51, T54 |
| T54 | T18, T50, T53, T102 |
| T55 | T56, T58, T91, T128 |
| T56 | T3, T55, T57, T60 |
| T57 | T2, T56, T59, T127 |
| T58 | T22, T41, T55, T101 |
| T59 | T23, T40, T57, T60 |
| T60 | T24, T56, T59, T98 |
| T61 | T62, T64, T73, T116 |
| T62 | T21, T61, T63, T66 |
| T63 | T20, T62, T65, T115 |
| T64 | T4, T35, T61, T105 |
| T65 | T5, T34, T63, T66 |
| T66 | T6, T62, T65, T110 |
| T67 | T68, T70, T79, T120 |
| T68 | T15, T67, T69, T72 |
| T69 | T14, T68, T71, T119 |
| T70 | T10, T29, T67, T109 |
| T71 | T11, T28, T69, T72 |
| T72 | T12, T68, T71, T106 |
| T73 | T61, T74, T76, T108 |
| T74 | T33, T73, T75, T78 |
| T75 | T32, T74, T77, T107 |
| T76 | T23, T40, T73, T113 |
| T77 | T22, T41, T75, T78 |
| T78 | T42, T74, T77, T118 |
| T79 | T67, T80, T82, T112 |
| T80 | T27, T79, T81, T84 |
| T81 | T26, T80, T83, T111 |
| T82 | T17, T46, T79, T117 |
| T83 | T16, T47, T81, T84 |
| T84 | T48, T80, T83, T114 |
| T85 | T49, T86, T88, T100 |
| T86 | T45, T85, T87, T90 |
| T87 | T44, T86, T89, T99 |
| T88 | T11, T28, T85, T121 |
| T89 | T10, T29, T87, T90 |
| T90 | T30, T86, T89, T126 |
| T91 | T55, T92, T94, T104 |
| T92 | T39, T91, T93, T96 |
| T93 | T38, T92, T95, T103 |
| T94 | T5, T34, T91, T125 |
| T95 | T4, T35, T93, T96 |
| T96 | T36, T92, T95, T122 |
| T97 | T40, T52, T98, T100 |

TABLE 2-continued

| T atom | Connected to: |
| --- | --- |
| T98 | T48, T60, T97, T99 |
| T99 | T3, T87, T98, T100 |
| T100 | T1, T85, T97, T99 |
| T101 | T46, T58, T102, T104 |
| T102 | T42, T54, T101, T103 |
| T103 | T9, T93, T102, T104 |
| T104 | T7, T91, T101, T103 |
| T105 | T28, T64, T106, T108 |
| T106 | T36, T72, T105, T107 |
| T107 | T15, T75, T106, T108 |
| T108 | T13, T73, T105, T107 |
| T109 | T34, T70, T110, T112 |
| T110 | T30, T66, T109, T111 |
| T111 | T21, T81, T110, T112 |
| T112 | T19, T79, T109, T111 |
| T113 | T16, T76, T114, T116 |
| T114 | T24, T84, T113, T115 |
| T115 | T27, T63, T114, T116 |
| T116 | T25, T61, T113, T115 |
| T117 | T22, T82, T118, T120 |
| T118 | T18, T78, T117, T119 |
| T119 | T33, T69, T118, T120 |
| T120 | T31, T67, T117, T119 |
| T121 | T4, T88, T122, T124 |
| T122 | T12, T96, T121, T123 |
| T123 | T39, T51, T122, T124 |
| T124 | T37, T49, T121, T123 |
| T125 | T10, T94, T126, T128 |
| T126 | T6, T90, T125, T127 |
| T127 | T45, T57, T126, T128 |
| T128 | T43, T55, T125, T127 | wherein the material contains a structure directing agent and part or all of the structure directing agent is removed.

20. The material of claim 19 having a micropore volume of 0.10 to 0.25 cc/g.

21. The material of claim 19 having a C-centered unit cell a-parameter of 17.9±0.5 Å, b-parameter of 21.4±0.5 Å, and c-parameter of 20.0±0.5 Å.

22. The material of claim 19, wherein the material is suitable for adsorbing 60 to 150 mg/g of n-hexane or 40 to 100 mg/g of mesitylene.

23. The material of claim 19 having the XRD peaks of:

| degree 2-theta (±0.2) | relative intensity [100 × I/(Io)] |
| --- | --- |
| 6.39 | 60-100 |
| 7.78 | 60-80 |
| 8.22 | 20-40 |
| 8.82 | 20-40 |
| 19.40 | 60-100 |
| 23.13 | 60-90 | and (i) has a micropore volume of 0.10 to 0.25 cc/g; (ii) has a C-centered unit cell a-parameter of 17.9±0.5 Å, b-parameter of 21.4±0.5 Å, and c-parameter of 20.0±0.5 Å; or (iii) is suitable for adsorbing 60 to 150 mg/g of n-hexane or 40 to 100 mg/g of mesitylene.

24. The material of claim 19 having Formula I:

(v)X$_2$O$_3$:YO$_2$  (Formula I), wherein 0.0005≤v≤0.1, X is a trivalent element, and Y is a tetravalent element.

25. The material of claim 24, wherein the molar ratio of Y to X is 5 to 25 when X is B.

26. The material of claim 24, wherein the molar ratio of Y to X is 100 to 500 when X is Al.

27. A structure directing agent compound having the following structure of Compound E:

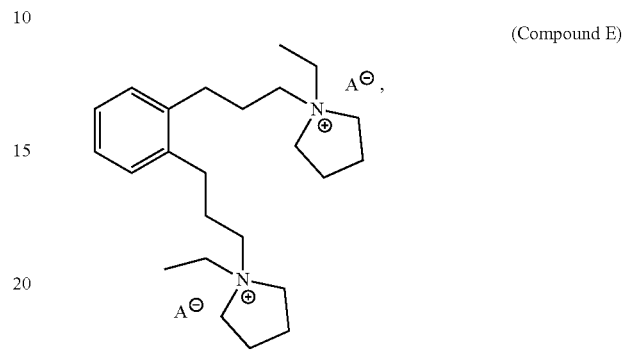

(Compound E)

wherein A is an ion.

28. A process of preparing Compound E of claim 27, wherein the process comprises converting Compound 7:

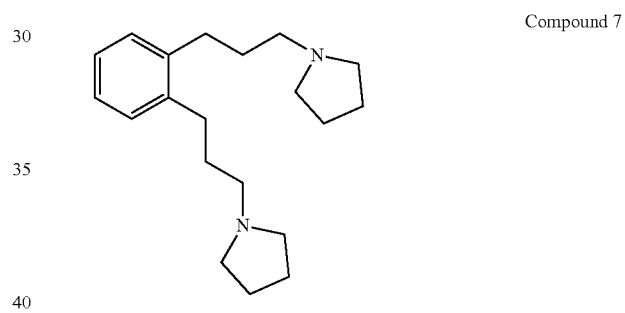

Compound 7 to Compound E.

29. A process of preparing Compound E of claim 27, wherein the process comprises converting Compound 6:

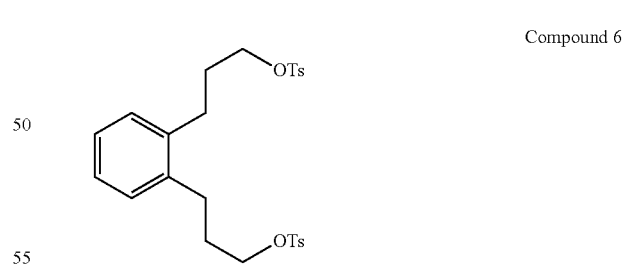

Compound 6 to Compound E, where T is a tosylate.

* * * * *